(12) United States Patent
Qu et al.

(10) Patent No.: US 10,954,489 B2
(45) Date of Patent: Mar. 23, 2021

(54) LIVER-MIMETIC DEVICE AND METHOD FOR SIMULATION OF HEPATIC FUNCTION USING SUCH DEVICE

(71) Applicant: THE REGENTS OF THE UNIVERSITY OF CALIFORNIA, Oakland, CA (US)

(72) Inventors: Xin Qu, Houston, TX (US); Maling Gou, Sichuan (CN); Wei Zhu, San Diego, CA (US); Shaochen Chen, San Diego, CA (US)

(73) Assignees: THE REGENTS OF THE UNIVERSITY OF CALIFORNIA, Oakland, CA (US); NATIONAL INSTITUTES OF HEALTH (NIH), U.S. DEPT. OF HEALTH AND HUMAN SERVICES (DHHS), Bethesda, MD (US)

( * ) Notice: Subject to any disclaimer, the term of this patent is extended or adjusted under 35 U.S.C. 154(b) by 707 days.

(21) Appl. No.: 14/895,912

(22) PCT Filed: Jun. 4, 2014

(86) PCT No.: PCT/US2014/040946
§ 371 (c)(1),
(2) Date: Dec. 3, 2015

(87) PCT Pub. No.: WO2014/197622
PCT Pub. Date: Dec. 11, 2014

(65) Prior Publication Data
US 2016/0298087 A1 Oct. 13, 2016

Related U.S. Application Data

(60) Provisional application No. 61/831,100, filed on Jun. 4, 2013, provisional application No. 61/927,906, filed on Jan. 15, 2014.

(51) Int. Cl.
*C12N 5/071* (2010.01)

(52) U.S. Cl.
CPC ........ *C12N 5/0671* (2013.01); *C12N 2506/45* (2013.01); *C12N 2533/30* (2013.01); *C12N 2533/54* (2013.01); *C12N 2533/80* (2013.01)

(58) Field of Classification Search
CPC .............. C12N 5/0671; C12N 2533/30; C12N 2533/80; C12N 2506/45
See application file for complete search history.

(56) References Cited

U.S. PATENT DOCUMENTS 7,219,016 B2   5/2007  Rimm et al.
2005/0169962 A1  8/2005  Bhatia et al.
2013/0337066 A1  12/2013  Zhang et al.

FOREIGN PATENT DOCUMENTS

CN         102114275 A     7/2011
WO    WO 2012071477 A2    5/2012

OTHER PUBLICATIONS

Tsang et al. "Fabrication of 3D hepatic tissues by additive photopatterning of cellular hydrogels" Faseb J 2007, 21, 790-801.*
Albrecht et al. "Probing the role of multicellular organization in three-dimensional microenvironments" Nature Methods, vol. 3, No. 5, May 2006, p. 375-375.*
Zorlutuna2 et al. "The Expanding World of Tissue Engineering: The Building Blocks and New Applications of Tissue Engineered Constructs," IEEE Reviews in Biomedical Engineering, vol. 6, p. 47-62, Dec. 20, 2012.*
Sullivan, et al., "Generation of Functional Human Hepatic Endoderm from Human iPS cells," Hepatology, Jan. 11, 2010, vol. 51, pp. 329-335.
Gauvin et al., "Microfabrication of complex porous tissue engineering scaffolds using 3D projection stereolithography," Biomaterials, May 2012, 33(15): 3824-3834.
Ma et al., "Vesicular Polydiacetylene Sensor for Colorimetric Signaling of Bacterial Pore-Forming Toxin," American Chemical Society Journal, Jun. 11, 2005, vol. 21, No. 14, pp. 6123-6125.
Aldridge et al., "Human Mesenchymal Stem Cells are Recruited to Injured Liver in a β1-Integrin and CD44 Dependent Manner," Hepatology, Sep. 2012, vol. 56, No. 3, pp. 1063-1073.
Chen, Shaochen, "Advanced Laser Manufacturing of Polymeric Nanocomposites," Office of Naval Research YIP Grant No. N00014-04-1-0568 Final Project Report, The University of Texas at Austin, Jul. 2007, pp. 1-10.
Gauvin et al., "Microfabrication of complex porous tissue engineering scaffolds using 3D projection stereolithography," Biomaterials, vol. 33, 2012, pp. 3824-3834.
Gou et al., "Bio-inspired detoxification using 3D-printed hydrogel nanocomposites," Nature Communications, May 8, 2014, 5:3774, pp. 1-9.
Hribar et al., "Light-assisted direct-wire of 3D functional biomaterials," Lab Chip, 2014, 14, pp. 268-275.
Soman et al., "A three-dimensional polymer scaffolding material exhibiting a zero Poisson's ratio," Soft Matter, 2012, 8, pp. 4946-4951.
Soman et al., "Digital microfabrication of user-defined 3D microstructures in cell-laden hydrogels," Biotechnology and Bioengineering, Jun. 3, 2013, vol. 110, No. 11, pp. 1-11.

(Continued)

*Primary Examiner* — Blaine Lankford
(74) *Attorney, Agent, or Firm* — Eleanor Musick; Musick Davison LLP

(57) ABSTRACT

A liver-mimetic device and method include a 3D polymer scaffold having a matrix of liver-like lobules with hepatic-functioning particles encapsulated within the lobules. In some embodiments, each liver-like lobule is hexagonal in structure and the matrix is in a honeycomb arrangement. In some embodiments, the hepatic-functioning particles are hepatic progenitor cells. In other embodiments, the hepatic-functioning particles are polymer nanoparticles adapted to capture pore-forming toxins.

28 Claims, 20 Drawing Sheets

(56) References Cited

OTHER PUBLICATIONS

Zorlutuna et al. "Microfabricated biomaterials for engineering 3D tissues," Advanced Materials, Mar. 13, 2012, vol. 24 No. 14, pp. 1782-1804.
PCT/US2014/0409435, International Search Report, dated Nov. 17, 2014, 10 pgs.

* cited by examiner

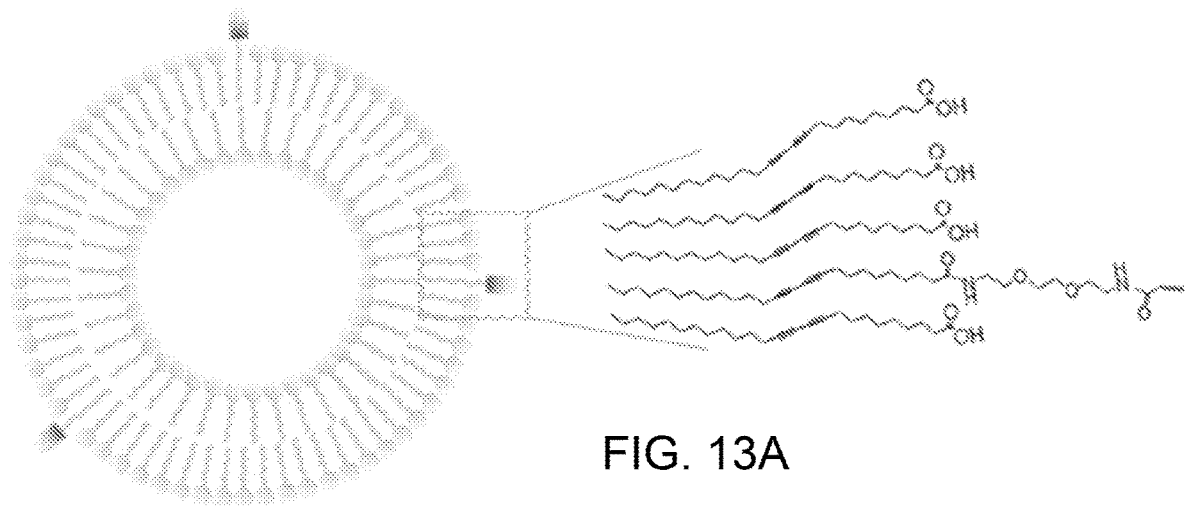
FIG. 13A
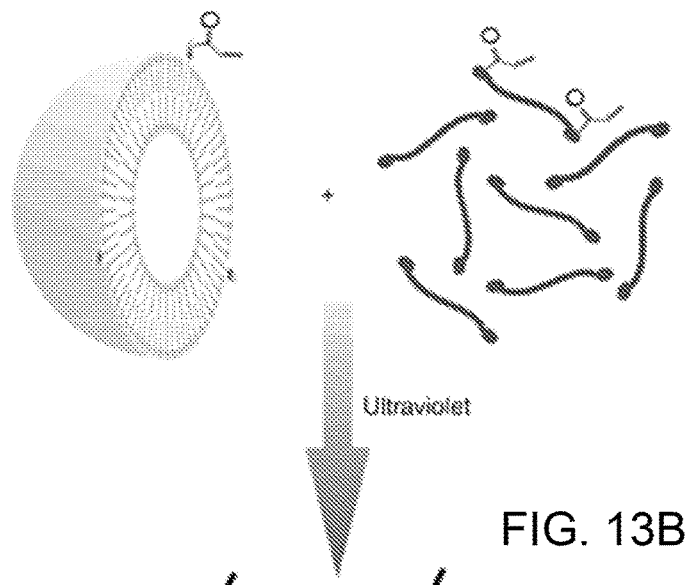
FIG. 13B
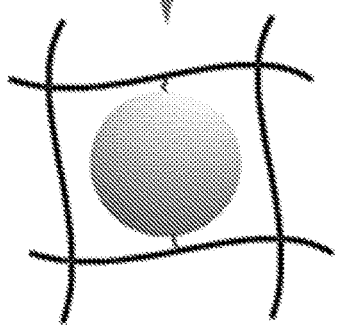

LIVER-MIMETIC DEVICE AND METHOD FOR SIMULATION OF HEPATIC FUNCTION USING SUCH DEVICE

RELATED APPLICATIONS

This application is a 371 national stage filing of International Application No. PCT/US2014/040946, filed Jun. 4, 2014, which claims the benefit of the priority of U.S. Provisional Application No. 61/831,100, filed Jun. 4, 2013 and U.S. Provisional Application No. 61/927,906, filed Jan. 15, 2014.

GOVERNMENT RIGHTS

This invention was made with government support under Grant EB017876 awarded by the National Institutes of Health. The government has certain rights in the invention.

FIELD OF THE INVENTION

The present invention relates to a liver-mimetic device fabricated using a 3D printed hydrogel matrix for encapsulating particles capable of performing hepatic functions and a method for simulation of hepatic function with a liver-mimetic device.

BACKGROUND

In the U.S., liver associated diseases are major contributors to morbidity and mortality. Approximately 40,000 people in the U.S. die each year from acute or chronic liver diseases. Organ transplantation is the gold standard of care for end-stage liver disease. Unfortunately, the dramatic discrepancy between available donors vs. patients on the waiting lists highlights the critical need for functional liver replacements. Furthermore, as the liver serves a vital role in drug metabolism and detoxification, the investigation of liver-drug interactions is an essential component of any preclinical drug study. Conventional animal models are costly, often unreliable, and difficult to translate to human studies due to the species-specific variations in hepatocellular functions. For example, in 2004, the FDA estimated that 92 out of every 100 drugs that successfully passed preclinical animal testing failed in subsequent human trials. The resulting financial consequences of a drug failing at the clinical stage can be catastrophic to the drug makers. While several human liver models, such as liver slices, microsomes, cell lines and primary hepatocytes, are currently in use, these models are still limited in terms of fully representing the dynamic cellular responses of healthy liver tissue.

Over the last two decades, liver tissue engineering has made significant progress towards the creation of in vitro liver models for drug screening, as well as in vivo constructs for ultimately addressing the large clinical need for transplant sources. Nonetheless, cell sourcing remains a significant challenge for both in vivo and in vitro liver models. Most tissue engineered liver models consist of suboptimal cell sources, such as primary hepatocytes and hepatic cell lines isolated from liver tumors (e.g. HepG2), which make them less practical for clinical applications. Current in vitro liver models includes liver slices, immortalized hepatic cell lines, primary hepatocyte cultures, multi-well perfused bioreactors, microfluidic devices (e.g., the cell-based hepatic models from HμREL® Corporation), and hollow fiber reactors. However, none of these models exhibit similar micro-architecture compared to native liver tissue. For instance, although HepG2 cells show great proliferative capacity and are relatively inexpensive, they display abnormal cellular functions when compared with native physiology. Moreover, the tumor origin of HepG2 cells presents a safety concern for in vivo applications. Conventional cultures of primary hepatocytes have served as the gold standard for in vitro applications, however, these primary cells lack robust proliferative capacity and are prone to de-differentiate fairly quickly. As a result, their functional activity can only be maintained for a relatively short time frame (i.e., 24-72 hours). Furthermore, human primary hepatocytes are difficult to obtain on a consistent basis.

Due to these limitations in sourcing optimal cell types, recent developments in iPSC (induced pluripotent stem cell) technology have attracted significant attention within the tissue engineering field due to the iPSC's competent proliferative capacity, proven pluripotency, and absence of ethical issues associated with embryonic stem cells (ESCs). Human iPSCs may provide a limitless supply of hepatocytes from multiple donors and thereby improve experimental reproducibility while also allowing for the investigation of individual-specific hepatotoxicity. Although there are limited data on the clinical safety of iPSCs, the development of patient-specific tissue and organ models from iPSCs would help bring to reality the vision of personalized in vitro organoid systems. Furthermore, these technologies can enable the design of disease-on-a-chip models for use as early-stage testing tools to assess pharmacotoxicity and therapeutic target engagement.

Improvements in cell sourcing notwithstanding, the development of fully functional liver constructs has been limited due to the challenge of fully recapitulating the native physical structure of hepatic tissue. Such micro-architecture plays a critical role in stem cell biology and hepatocellular function. Replicating these tissue morphologies involves the consideration of both their complex 3D geometries as well as the heterogeneity of their constituent cell populations. Numerous groups have demonstrated the substantial difference in cellular physiology between 2D vs. 3D culture systems. Likewise, co-culture of multiple cell types can direct markedly different cell activity as compared with monoculture. Endothelial cells can help stabilize hepatocytes and participate in blood vessel formation. MSCs have shown great potential in inhibiting hepatocyte apoptosis and supporting hepatocellular function. However, very limited progress has been achieved in fully mimicking the native architecture and organization of liver in both composition and form, partially due to the lack of appropriate biofabrication techniques.

Focusing specifically on the important hepatic function of detoxification, pore-forming toxins (PFTs) that can damage cellular membrane are key virulence factors of pathologies resulting from animal bites/stings and bacterial infections. Conventional detoxification platforms such as antisera, monoclonal antibodies and small-molecule inhibitors are unable to completely neutralize toxins because of their limited ability to block the entire PFT molecule. In addition, over 80 PFTs have been identified, displaying diverse molecular structures and distinctive epitopic targets. The commonly used antidotes target the specific molecular structures of PFTs. Thus, customized treatments are frequently required for different toxins.

Due to their inherent small size and flexibility in rational design and preparation, functional nanoparticles have shown potential applications in effective detoxification. Recent advancements in the field have spurred the development of nanoparticles that can efficiently bind PFTs and neutralize their toxicity in vivo. Although patients suffering from poisoning may benefit from these strategies, intravenous administration of nanoparticles can cause nanoparticle-toxin accumulation in the liver, leading to the risk of secondary poisoning, which is particularly detrimental in liver-failure patients. Despite these challenges, cleaning blood by adsorption of toxins to retrievable nanoparticles provides an alternative strategy for detoxification. Meanwhile, similar to injection of antidotes, it is clinically approved to remove toxins by in vitro devices.

SUMMARY OF THE INVENTION

According to embodiments of the invention, dynamic optical projection stereolithography ("DOPsL") is used for rapid, scalable fabrication of highly-specified biomimetic structures. In particular, a 3D liver-mimetic structure can be fabricated using DOPsL to closely mimic hepatic micro-architecture and function by encapsulating particles that are capable of performing one or more liver function. These particles can be cells or polymer nanoparticles.

In some embodiments, a functional in vitro micro-liver model can be produced via encapsulation of hepatic progenitor cells (HPCs) derived from human iPSCs using dynamic optical projection stereolithography ("DOPsL"). This advanced model consists of co-culture of HPCs and supportive cells (endothelial cells and mesenchymal stem cells) within a biomimetic scaffold closely mimicking hepatic micro-architecture. This patient specific liver-on-a chip model can be explored as a reliable and cost-efficient in vitro platform to facilitate drug metabolism studies, preclinical drug screening, and fundamental hepatology research.

In a preferred embodiment, hepatic progenitor cells derived from human iPSCs are used instead of primary hepatocyte and immortalized hepatic cell lines. In addition, patient specific iPSCs, which could enable personalized in vitro disease models, are also available from patients with certain diseases that affect the liver, such as cancer or glycogen storage disease type I.

In other embodiments, polydiacetylene (PDA) nanoparticles are used to attract, capture and sense PFTs by installing the nanoparticles in a biomimetic hydrogel matrix formed by printing via dynamic optical projection stereolithography to create a precise 3D matrix with a modified liver lobule configuration.

The DOPsL technology utilizes a digital mirror array device (DMD) to generate dynamic photomasks that can be translated into a 3D complex structure through layer-by-layer photopolymerization of biomaterials. The DOPsL technology has demonstrated considerable versatility in fabricating 3D complex geometries for functional devices and even artificial tissues, providing for the rapid and scalable fabrication of highly-specified biomimetic structures. This approach provides capability in terms of speed and scalability that cannot be well-achieved using existing technologies that employ raster-based printing approaches or soft lithography techniques. Additionally, as the DOPsL system can accept any set of high detail images, this platform provides a method for generating models with patient specificity not only in terms of cell type but also whole tissue morphology. Furthermore, the flexibility of the platform allows for the modular addition and subsequent decoupling of various components of a complex 3D construct, providing a means to determine the individual contributions of material type, co-culture populations, spatial cell arrangements, and biomimetic geometry towards recapitulating native liver physiology. Using the DOPsL approach, appropriate liver-on-a-chip models can be fabricated for various application contexts from fundamental hepatic functionality to high throughput screening for pharmacotoxicity.

Utilizing biofabrication, a 3D matrix can be formed with a modified liver lobule configuration to encapsulate nanoparticles and/or cells that possess hepatic function. This liver-on-a-chip in vitro model provides a tool for a variety of applications. In addition to detoxification, the device may also serve as a versatile instrument for cost-effective and reliable early-stage drug targeting and preclinical drug screening. Such a device has the potential of markedly reducing the high cost of drug development, now a major economical roadblock to sustained progress in healthcare.

In one aspect of the invention, a liver-mimetic device includes a 3D polymer scaffold comprising a matrix of liver-like lobules with hepatic-functioning particles encapsulated within the lobules. In some embodiments, each liver-like lobule is hexagonal in structure and the matrix is in a honeycomb arrangement. In a first embodiment, the hepatic-functioning particles are hepatic progenitor cells, which may be derived from human induced pluripotent stem cells (iPSCs). The iPSCs may be patient specific, and may be from subjects having a liver-affecting disease. The hepatic-functioning particles may further comprise supportive cells, which may include mesenchymal stem cells and endothelial cells. The 3D polymer scaffold may be formed from a methacrylated hyaluronic acid or a gelatin methacrylate prepolymer polymerized using dynamic optical projection stereolithography.

In other embodiments, the hepatic-functioning particles are polymer nanoparticles adapted to capture pore-forming toxins. The polymer nanoparticles may be polydiacetylene, and the 3D polymer scaffold may be formed from poly (ethylene glycol) diacrylate hydrogel polymerized using dynamic optical projection stereolithography. In a preferred embodiment, the polymer nanoparticles are chemically tethered to the 3D polymer scaffold.

In another aspect of the invention, a liver-mimetic device is provided comprising: a 3D polymer scaffold comprising a matrix of liver-like lobules; and hepatic progenitor cells encapsulated within the lobules. Each liver-like lobule may be hexagonal in structure and the matrix is in a honeycomb arrangement. In certain preferred embodiments, the hepatic progenitor cells may be derived from human induced pluripotent stem cells (iPSCs), which may be patient specific and from subjects having a liver-affecting disease. Supportive cells, including mesenchymal stem cells and endothelial cells, may be encapsulated within the lobules. The 3D polymer scaffold may be formed from a methacrylated hyaluronic acid or gelatin methacrylate prepolymer polymerized using dynamic optical projection stereolithography.

In still another aspect of the invention, a liver-mimetic device is provided comprising:3D polymer scaffold comprising a matrix of liver-like lobules with polymer nanoparticles encapsulated within the lobules, wherein the polymer nanoparticles are adapted to capture pore-forming toxins. Each liver-like lobule may be hexagonal in structure and the matrix is in a honeycomb arrangement. In certain preferred embodiments, the polymer nanoparticles are polydiacetylene. The 3D polymer scaffold may be formed from poly (ethylene glycol) diacrylate hydrogel polymerized using dynamic optical projection stereolithography. The polymer nanoparticles are preferably chemically tethered to the 3D polymer scaffold.

In yet another aspect of the invention, a method is provided for in vitro simulation of a hepatic function on a material by photopolymerizing a prepolymer to form a 3D polymer scaffold comprising a matrix of liver-like lobules; encapsulating hepatic-functioning particles within the matrix; and exposing the matrix and hepatic-functioning particles to the material. The step of photopolymerizing comprises using dynamic optical projection stereolithography. Each liver-like lobule is generally hexagonal in structure and the matrix is in a honeycomb arrangement. In some embodiments, the hepatic-functioning particles comprise hepatic progenitor cells, which may be derived from human induced pluripotent stem cells (iPSCs) that are patient specific. The hepatic-functioning particles may further comprise mesenchymal stem cells and/or endothelial cells. The prepolymer may be a methacrylated hyaluronic acid or a gelatin methacrylate. In other embodiments, the hepatic-functioning particles comprise polymer nanoparticles adapted to capture pore-forming toxins. The polymer nanoparticles may be polydiacetylene. The prepolymer may comprise poly(ethylene glycol) diacrylate hydrogel, and the polymer nanoparticles may be chemically tethered to the 3D polymer scaffold. The hepatic function may comprise detoxification and the material is blood or blood cells.

BRIEF DESCRIPTION OF THE DRAWINGS

FIG. 9B is a photograph of centrifuged RBCs after incubation with normal saline (control) or melittin (5 μg/mL) mixed with different concentrations of PDA nanoparticles; FIG. 9C is a plot of the quantified efficiency of neutralizing the hemolytic activity of melittin (5 μg/mL) by PDA nanoparticles; FIG. 9D is a plot of intensity of red fluorescence (550 nm) of PDA nanoparticles (20 μg/mL) exposed to different concentrations of melittin. FIG. 9F plots the preventative absorption curves of initial PDA nanoparticles (blue) and melittin incubated PDA nanoparticles.

FIG. 11A shows simulation results obtained by docking PDA to melittin where I shows the conformation of the complex composed of PDA and melittin. Groups which take part in electrostatic interaction were marked; II shows PDA under the interface. Polar heads and hydrophobic tails which interact with melittin are represented with stick; and shows melittin above the interface. Atoms which interact with PDA are represented with scaled ball and stick and carbon atoms are colored with dark green. FIG. 11B shows simulated interactions between PDA and melittin studied by performing simulated annealing using molecular dynamics. FIG. 11C illustrates PDA-melittin interaction mode obtained by performing simulated annealing using molecular dynamics, where I shows PDA on the interaction interface; and II shows the interaction mode of melittin to PDA.

FIGS. 13A-13C show the preparation of PCDA-A and PCDA mixed nanoparticles, where FIG. 13A illustrates a schematic presentation of the surface groups of PCDA-A and PCDA mixed nanoparticles. By mixing PCDA and PCDA-A, the resulting nanoparticles possessed some acrylamide group on its surface. FIG. 13B provides a schematic presentation of installing PDA nanoparticles in the network of PEGDA hydrogel. PDA nanoparticles can be chemically linked to the network of PEGDA hydrogel by photocrosslinking PEGDA monomer and acrylamide modified PDA nanoparticles via addition polymerization. FIG. 13C is a SEM image of PCDA-A and PCDA mixed nanoparticles. The scale bar is 1 μm.

DETAILED DESCRIPTION OF EMBODIMENTS OF THE INVENTION

According to embodiments of the invention, a functional in vitro micro-liver model can be fabricated using a 3D printing technique for formation of hydrogel matrix with a liver-mimetic structure. The matrix is loaded with particles adapted to biologically or chemically neutralize toxins and/or perform other hepatic functions.

Such materials may include hepatic progenitor cells (HPCs) (e.g., FIG. 1) or nanoparticles (see, e.g., FIG. 2) that attract, sense and capture toxins.

As used herein, a "hepatic-functioning particle", or "HFP", means a biological or chemical particle that may be encapsulated, installed or otherwise fixed within a 3D matrix having a liver lobule-like configuration and which perform one or more hepatic functions, which may include detoxification to collect and neutralize toxins. Non-limiting examples of biological particles are hepatocytes, hepatic progenitor cells, also known as intrahepatic stem cells. Chemical particles may include polymers in particulate form, and particularly nanoparticles.

Figure 1A:
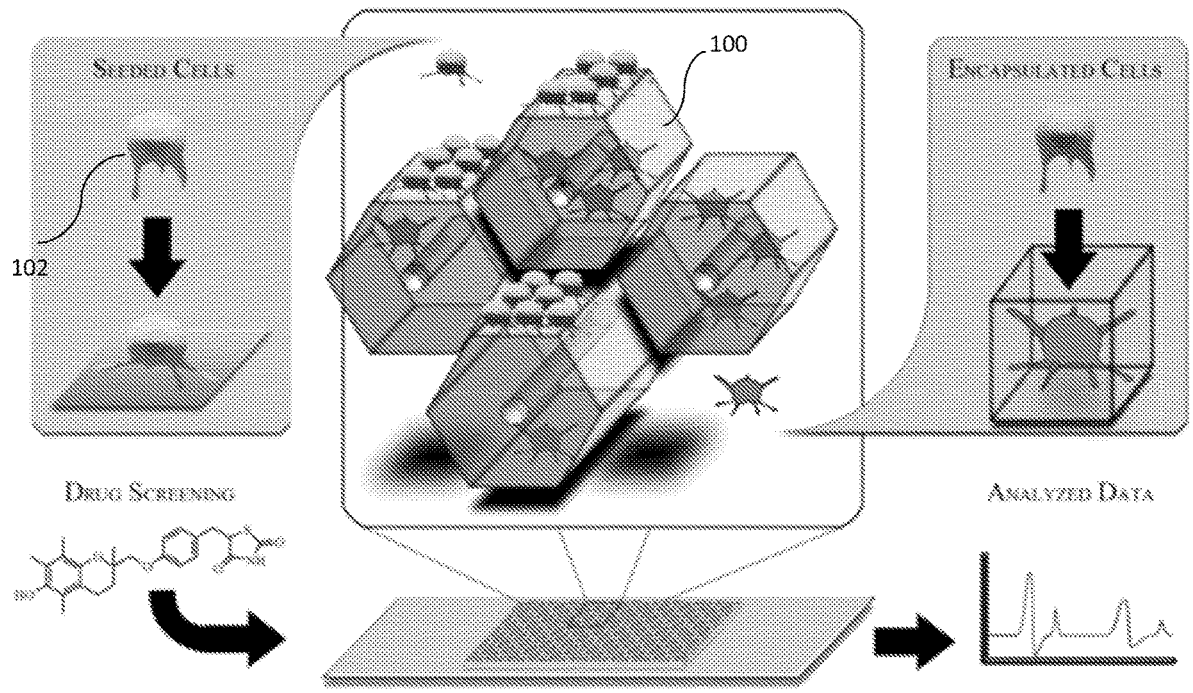
FIG. 1A is a schematic diagram of an exemplary 3D liver-mimetic device with encapsulated cells for providing hepatic function.
Figure 1B:
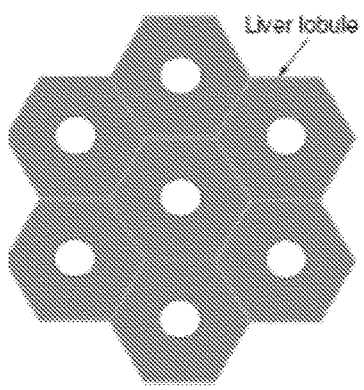
FIG. 1B is a diagram showing the structure of a liver.
Figure 1C:
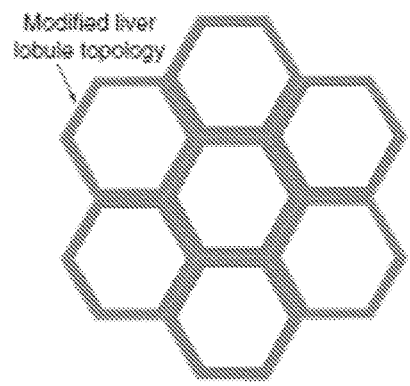
FIG. 1C is a diagram showing the liver-mimetic structure according to the invention.

FIG. 1A illustrates one embodiment of the inventive 3D liver-mimetic device with encapsulated cells as hepatic-functioning particles (HFPs). The 3D matrix is formed by using dynamic optical projection stereolithography to spatially pattern hepatic progenitor cells (HPCs) 102 suspended in a prepolymer solution to form a polymer scaffold 100 that mimics hepatic lobules. The liver has a hexagonal lobule structure centered around the terminal hepatic vein, which helps to efficiently remove waters and xenobiotics from the system (FIG. 1B). To simulate actual liver function, the inventive liver-mimetic structure may be designed to allow the toxins to reach the center of the matrix quickly, as shown in FIG. 1C, by forming a matrix of hexagonal structures having dimensions selected to optimize exposure of the HFP to the blood. The hexagonal structures, or "liver-like lobules," are assembled to create a complex honeycomb-like structure.

Figure 2:
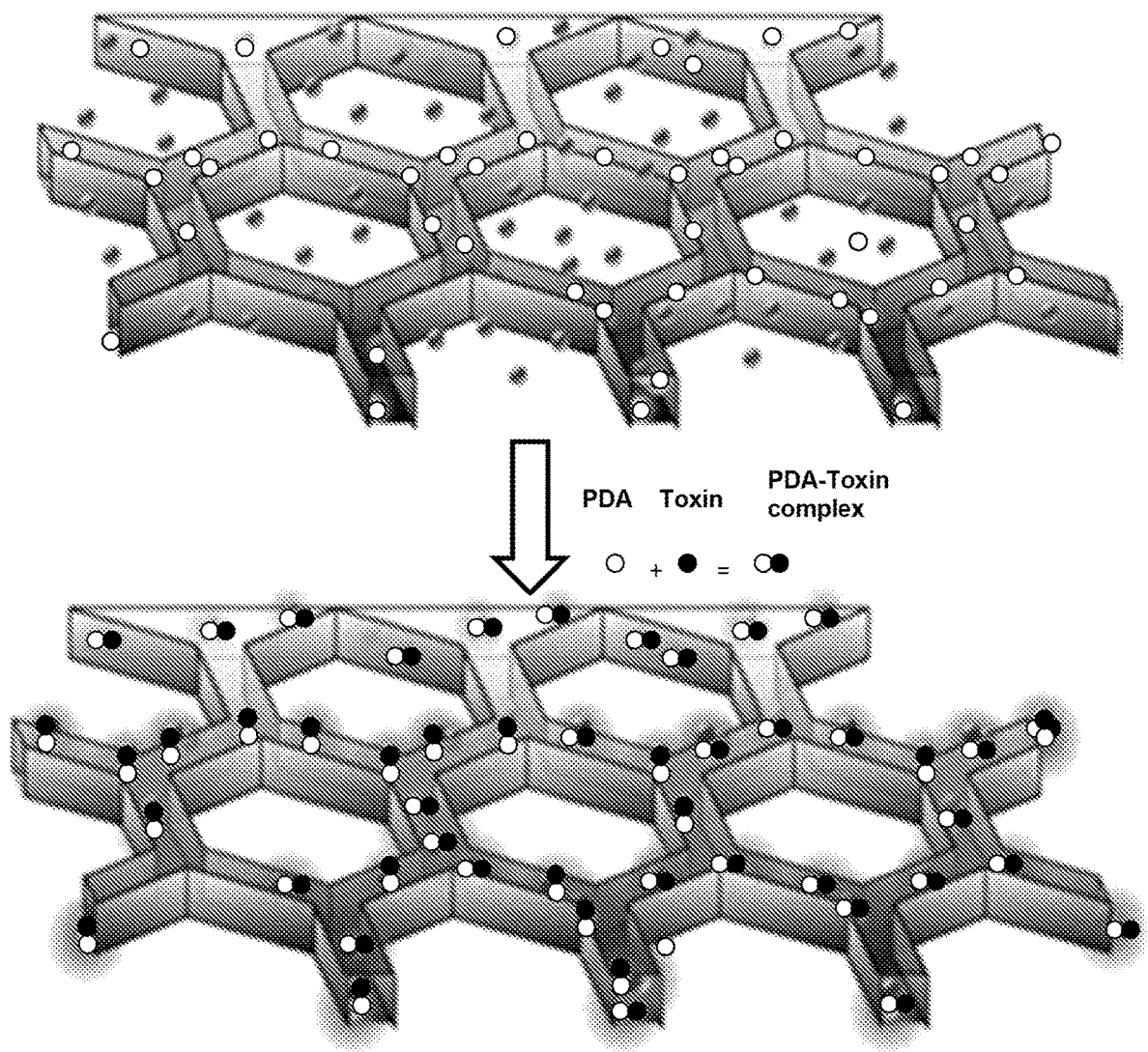
FIG. 2 is a schematic diagram of another embodiment of a 3D liver-mimetic device incorporating PDA nanoparticles to attract, capture and sense toxins.

FIG. 2 illustrates another embodiment of the 3D liver-mimetic device in which a matrix of hexagonal lobular structures is loaded with exemplary hepatic-functioning particles (HFPs), namely polydiacetylene (PDA) nanoparticles, which are indicated by the white circles. The toxins are represented by the dark spheres or circles. As shown in the lower portion of the figure, the PDA nanoparticles have attracted and trapped the toxins to form a PDA-toxin complex.

Figure 3A:
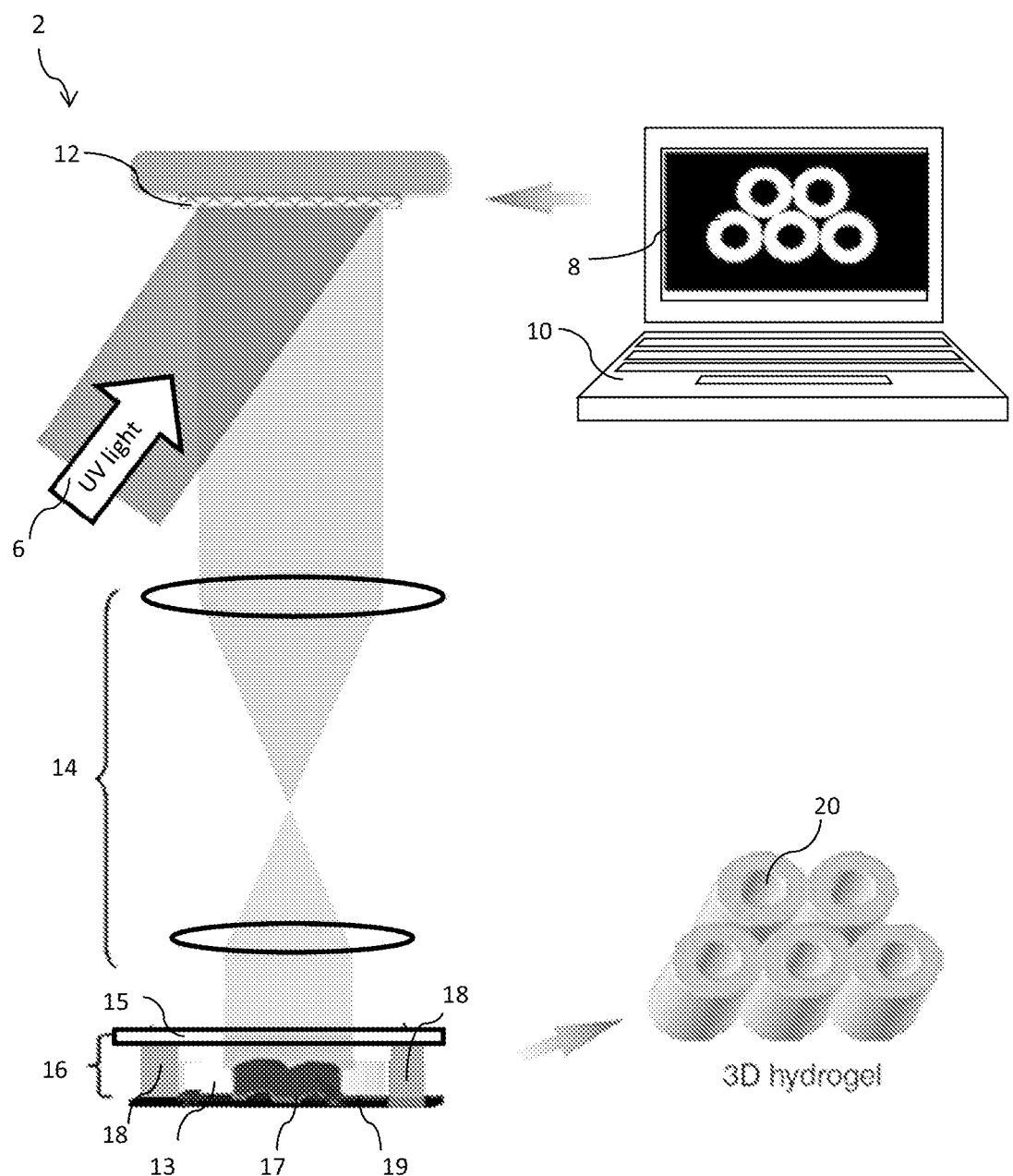
FIG. 3A is a schematic diagram of an exemplary dynamic optical projection stereolithography (DOPsL) system.

Fabrication of a 3D liver-mimetic hydrogel matrix employs digital mask (i.e.,"maskless") projection printing in which a digital micro-mirror device (DMD) found in conventional computer projectors to polymerize and solidify a photosensitive liquid prepolymer using ultraviolet (UV) or other light sources appropriate for the selected polymer. FIG. 3A illustrates an exemplary implementation of a maskless projection printing system 2, referred to as the "dynamic optical projection stereolithography" (DOPsL) platform. The "maskless" or digital mask approach allows for the use of controllable and interchangeable reflected light patterns rather than static, more expensive physical masks like those used in conventional photolithography. The system 2 includes a UV light source 6, a computer controller 10 for sliced image flow generation to guide creation of the pattern, a DMD chip 12, which is composed of approximately one million micro-mirrors, embedded in a projector as a dynamic mask, projection optics 14, a translation stage 16 for sample position control, and a source of photocurable prepolymer material 13. The DMD chip 12 acts an array of reflective coated aluminum micro-mirrors mounted on tiny hinges that enable them to tilt either toward the light source or away from it, creating a light ("on") or dark ("off") pixel on the projection surface, thus allowing it to redirect light in two states [0,1], tilted with two bias electrodes to form angles of either +12° or −12° with respect to the surface. In this way, a DMD system can reflect pixels in up to 1,024 shades of gray to generate a highly detailed grayscale image.

The computer controller 10 may display an image of the desired structure 8 for a given layer, as shown, and/or may display the desired parameters of the matrix. A quartz window or other light transmissive material 15, spacers 18, and base 19, all supported on the translation stage 16, define a printing volume or "vat" containing the prepolymer solution 13. Additional solution 13 may be introduced into the printing volume as needed using a syringe pump (not shown.) Based on commands generated by controller 10, the system spatially modulates collimated UV light using DMD chip 12 (1920×1080 resolution) to project custom-defined optical patterns onto the photocurable prepolymer solution 13.

Figure 3B:
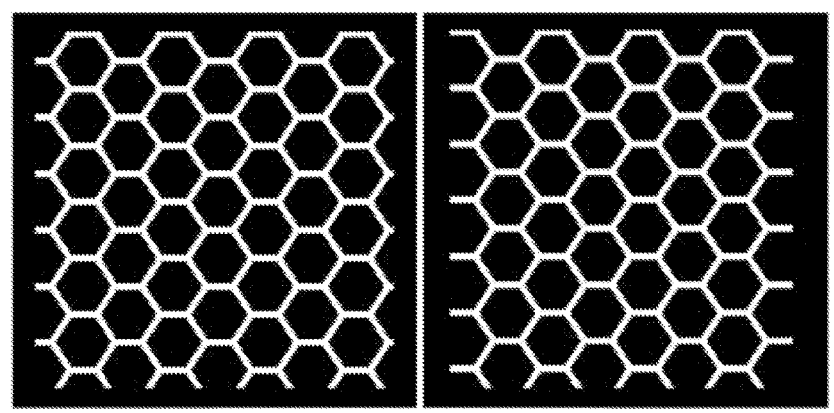
FIG. 3B is a diagram of two masks for printing a liver-mimetic structure using the system of FIG. 3A.

To generate 3D structures, projection stereolithography platforms such as DOPsL employ a layer-by-layer fabrication procedure. In an exemplary approach, a 3D computer rendering (made with CAD software or CT scans) is deconstructed into a series of evenly spaced planes, or layers. The pattern for each layer is displayed on the DMD chip 12, exposing UV light onto the photocurable material 13 to create polymer structure 17. After one layer is patterned, the computer controller 10 lowers the automated stage 16 and the next pattern is displayed to build the height of the polymer structure 17. Through programming of the computer controller 10, the user can control the stage speed, light intensity, and height of the structure 17, allowing for the fabrication of a variety of complex structures, e.g., completed structure 20. FIG. 3B illustrates exemplary masks that may be used for printing a liver-mimetic 3D structure with hexagonal lobules for use in a device incorporating HFPs. As can be seen from the figure, these masks, each of which has a honeycomb-like pattern, are slightly offset from each other, providing for printing of layers that are similarly offset. By alternatively using the left and right masks in DOPsL technology, a bio-inspired device with multiple layers of liver-mimetic structure can be created. In an evaluation device, four layers were formed. The masks, which can be created on a "PowerPoint-like" slide, can be dynamically altered as per the CAD model to design and fabricate a wide variety of 3D features. An important advantage of this system is that it does not use any organic solvents that may otherwise compromise the biocompatibility of the scaffold material. The DOPsL technology is ideal for high-throughput fabrication and is easily scalable, an essential quality for generating high-volume screening platforms.

Figure 3C:
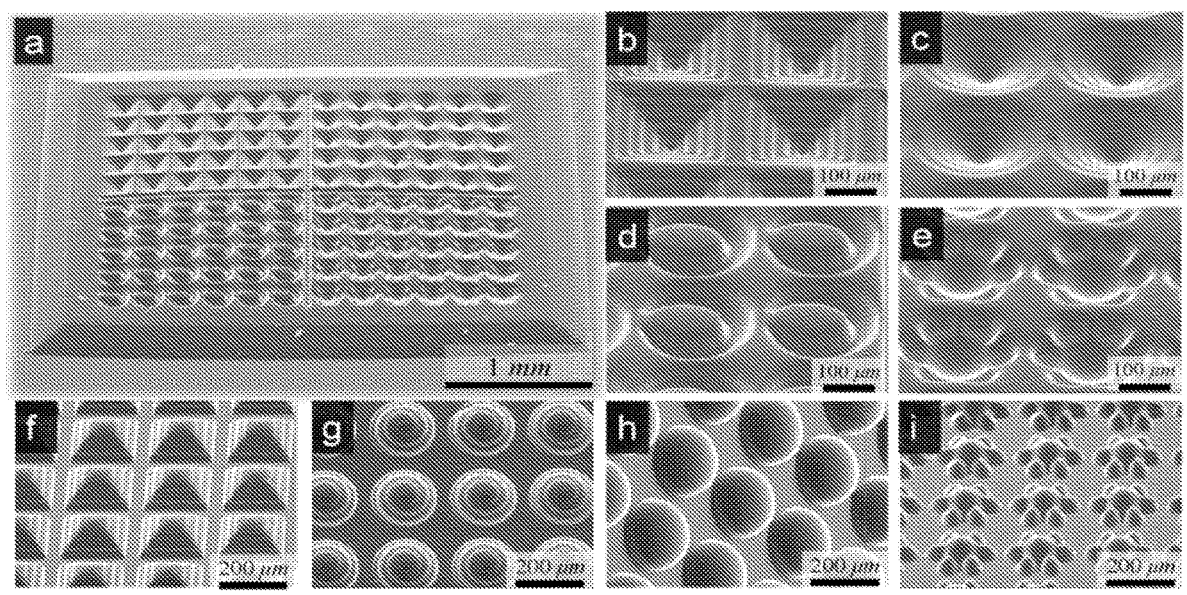
FIG. 3C is a set of SEM images of complex geometries created using DOPsL.
Figure 3D:
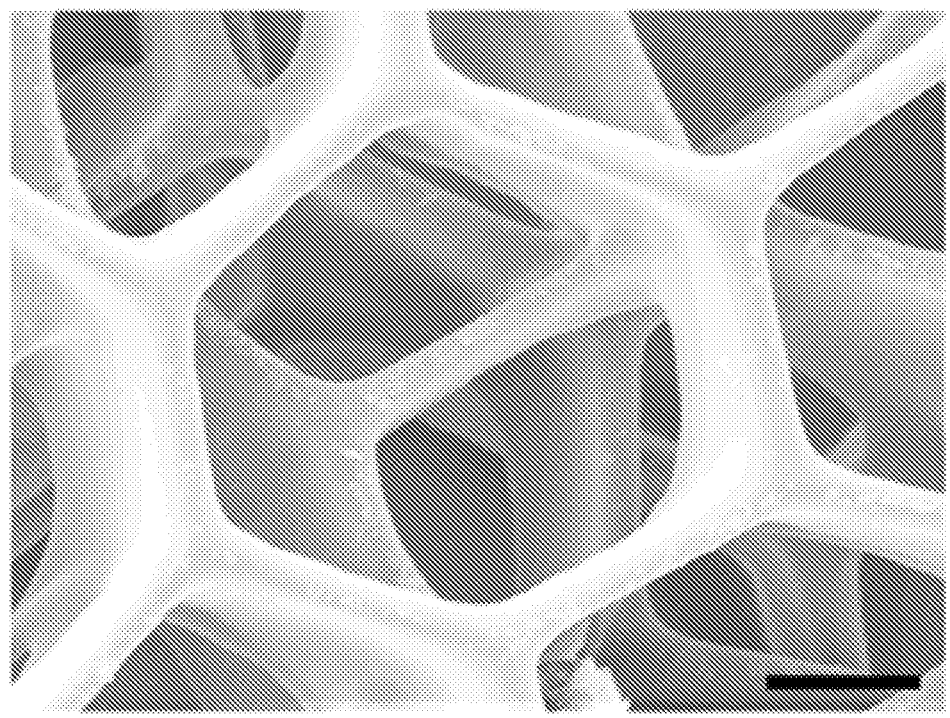
FIG. 3D is a SEM image of an exemplary liver-mimetic structure fabricated using DOPsL and the masks of FIG. 3B.

FIG. 3C provides a number of examples of structures that have been formed using DOPsL. The SEM micrographs in FIG. 3C show (a) a variety of PEG microwells with complex geometries such as: (b) steps, (c) spiral, (d) embryo-like, and (e) flower-like shapes. Images (f)-(i) are the inverses of the microwells of (b)-(e), demonstrating the versatility of the DOPsL method. FIG. 3D is a SEM micrograph of an exemplary liver-mimetic structure as used in embodiments of the invention. As seen in the figure, the layers of the mask were offset in alternating layers to create a complex pattern.

The following description provides details of embodiments of the liver-mimetic device that utilize different hepatic functioning particles in conjunction with the 3D scaffold described above. The first exemplary embodiment uses hepatic progenitor cells with additional support cells; the second uses polydiacetylene nanoparticles.

Cells as HFPs

Figure 4:
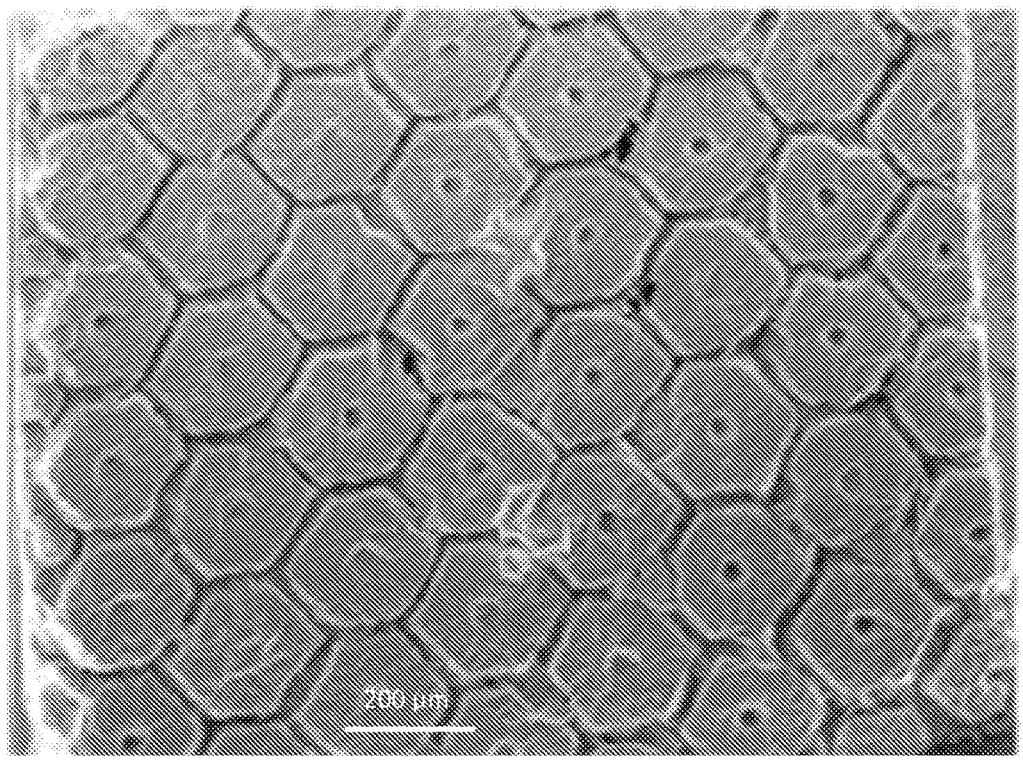
FIG. 4 is a SEM image of a fabricated biomimetic scaffold.

In the embodiment in which the HFPs include hepatic progenitor cells (HPCs), hepatic lobule structures are loaded onto the DOPsL system and fabricated to mimic the liver micro-architecture. FIG. 4 is a SEM image of one embodiment of fabricated biomimetic scaffold showing similar geometry to that of native liver tissue. The cells recognize and follow the geometry cues provided by the scaffold. In orthogonal views, cells can be observed aligning in the channels and the central conduit features, which were designed to mimic the blood vessel network in the liver tissue. (The scale bar in FIG. 4 is 200 microns.)

Two strategies may be employed to create a 3D micro-liver model using HPCs as HFPs. In the first approach, HPCs, mesenchymal stem cells (MSCs) and endothelial cells (ECs) are mixed and re-suspended in a prepolymer solution such as methacrylated hyaluronic acid (MeHA) or gelatin methacrylate (GelMA). The cell suspension is polymerized using the DOPsL platform as described above to generate a liver lobule pattern similar to that shown in FIG. 1C. In the multi-cell approach, all cells can maintain direct cell-cell interactions without establishing initial spatial control over cell types. Observations of cell migration and co-localization provide insight into the ability of these various cell types to self-organize. In the second approach, only HPCs are encapsulated into the 3D scaffold mimicking the hepatic lobule by using the same procedure as in described above. Supportive cells (i.e., MSCs, ECs) are seeded onto the scaffold later. In this latter approach, HPCs cannot initially form direct cell-cell interactions with the supportive cells. This approach may decouple the effects of cell-released factors versus direct cell-cell interactions. Furthermore, it allows tighter control of the 3D spatial localization of HPCs and supportive cells, which can better mimic the native tissue and also potentially facilitate cell isolation at a later time. The channel-like features in the scaffolds have shown promising results in inducing ECs to align into blood vessel-like structures and in stabilizing the interactions between ECs and mural cells.

Figure 5:
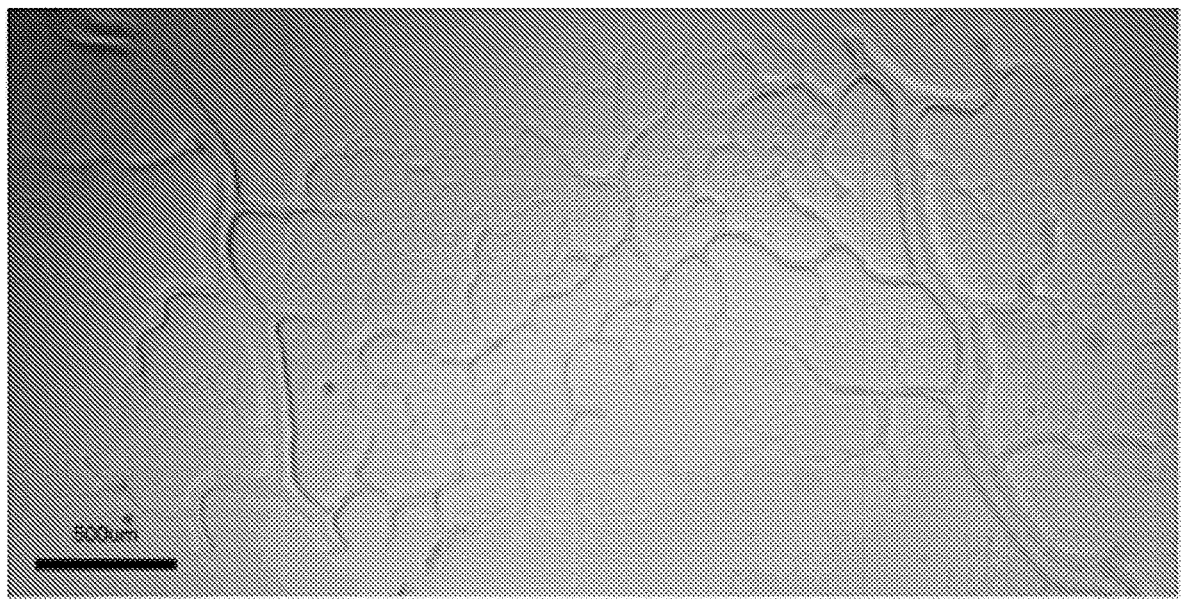
FIG. 5 shows the vasculature features replicated in GelMA via the DOPsL platform.
Figure 6:
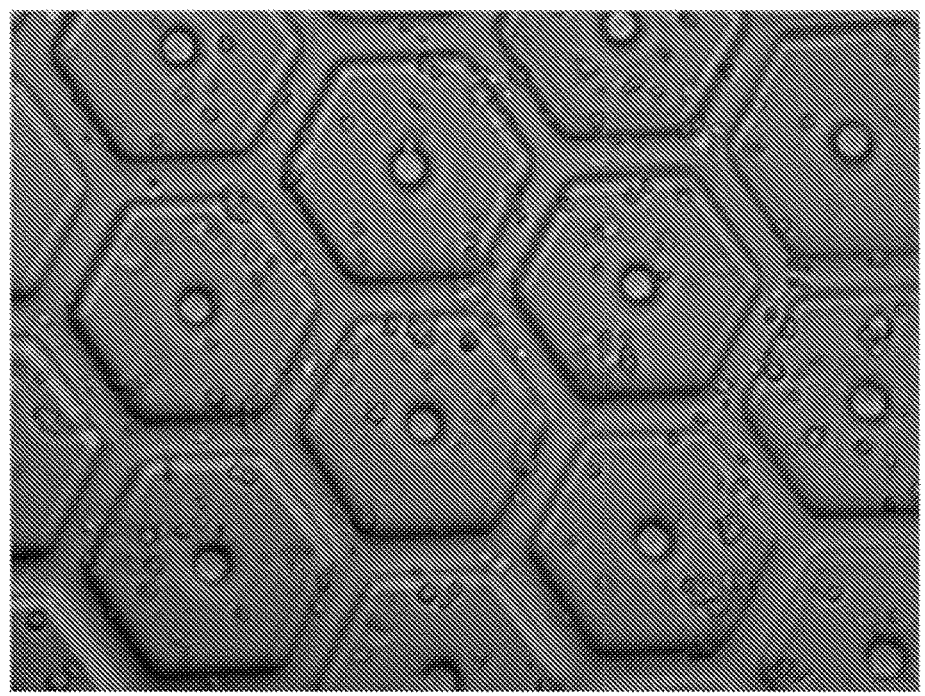
FIG. 6 shows MSCs encapsulated in a biomimetic scaffold for liver-on-a-chip using GelMA

FIG. 5 provides an example of vasculature features replicated in GelMA via the DOPsL platform. The pattern demonstrated high fidelity from 100 microns down to 10 microns. The scale bar in FIG. 5 represents 500 microns. FIG. 6 shows MSCs encapsulated in a biomimetic scaffold for liver-on-a-chip using GelMA.

A 3D hepatic culture model can be established in highly biomimetic scaffolds using progenitor cells derived from iPSCs. These embodiments employ technology developed by Allele Biotechnology and Pharmaceuticals, Inc. (San Diego, Calif., US) involving a highly efficient protocol to reprogram human fibroblasts back to iPSCs and differentiate them into multiple lineages, including hepatic progenitor cells (HPCs). This protocol is described in more detail by J. Wang et al. in International Publication No. WO2013/173248, entitled"Feeder-free derivation of human induced pluripotent stem cells with messenger RNA", which is incorporated herein by reference.

A co-culture system can be developed by incorporating additional supportive cell types, such as endothelial cells (ECs) and mesenchymal stem cells (MSCs). Endothelial cells have been demonstrated to preserve liver-specific functions in 3D culture. Additionally, MSCs co-cultured with hepatocytes can differentiate into hepatocyte-like phenotypes, and MSCs have drawn great attention as feeder cells for progenitor cells. Endothelial cells may be seeded into designated patterns mimicking the vasculature structures associated with native hepatic tissue. MSCs can be co-cultured with hepatocyte precursor cells in the scaffold to potentially facilitate hepatic function. Cell localization within this heterogeneous tri-culture model can be monitored by immunofluorescent staining and confocal microscopy.

For evaluation, iPSCs from Allele Biotechnology were used and reprogrammed via the above-described feeder-free, xeno-free protocol using messenger RNA to generate "footprint-free" iPSCs with efficiencies equaling or surpassing those attained through integration of viral vectors. In addition, patient specific iPSCs, which could enable creation of personalized in vitro disease models, are also available from patients with certain diseases, such as cancer and glycogen storage disease type I.

A growing body of literature has indicated that the cellular microenvironment can play a key role in hepatic culture. For instance, hepatocytes tend to de-differentiate rapidly within conventional 2D culture, whereas 3D cultures can maintain hepatic phenotype and function for substantially longer periods. Limited success has been achieved in 3D hepatic cultures that utilize simple configurations, such as slab and spheroid geometries, due to poor oxygen and nutrient diffusion. Optimization of the pore size of the scaffold can be used to overcome the diffusion barrier.

Figure 7:
FIG. 7 is a photomicrograph showing how iPSCs differentiate into hepatic progenitor cells (HPCs). The scale bar is 100 μm.

Three different human iPSCs lines (from healthy donors and cancer patients), reprogrammed with Allele Biotech's 6-Factor M30 mRNA Mix in a feeder-free and xeno-free culture system were used. These cells are directed to hepatic differentiation via a newly modified four-step protocol utilizing chemicals and growth factors. Briefly, iPSCs are seeded at a density to reach 50% confluence in vitronectin-coated plates with TeSR2 complete medium. From day 1 to day 5, as the cells reach full confluence, cells are directed to definitive endoderm (DEs) with CHIR99021 (GSK3β inhibitor) and LY294002 (PI3K inhibitor) in TeSR2 basal medium, followed by application of 1% DMSO in TeSR2 basal medium from day 5 to day 9 to direct DE to hepatic progenitor cells (HPCs). Finally, HPCs are then harvested, seeded within the 3D structures, and further directed to hepatocyte maturation via the addition of hepatocyte growth factor (HGF) and oncostatin M (OSM) in the hepatocyte medium. FIG. 7 is a SEM micrograph showing iPSCs differentiating into hepatic progenitor cells (HPCs). During the differentiation process, the iPSCs went through a series of profound morphological changes, and hepatocyte morphology started emerging from day 8. By day 10, HPCs with characteristic hepatocyte morphology (polygonal in shape, with distinct round nuclei) were harvested and seeded at low cell density to prevent over-differentiation before they were introduced into the 3D structure for hepatic maturation.

Scaffold fabrication parameters including curing depth, curing uniformity, and spatial resolution in x, y, and z can be optimized by varying exposure times and UV intensities. In some embodiments, methacrylated hyaluronic acid (MeHA) and gelatin methacrylate (GelMA) are used to form the 3D scaffolds. Hyaluronic acid (HA), a naturally derived non-sulfated glycosaminoglycan, is an essential component of the extracellular matrix and can be found throughout the body. HA and its derivatives have been widely used in biomedical and clinical applications due to their superior biocompatibility and important roles in many cellular responses, such as cell signaling, wound healing, and morphogenesis. By optimizing the methacrylation process, the methacrylation ratio of the HA can be controlled. Combined with a selection of HA molecular weights, a broad range of mechanical properties can be tuned to meet specific requirements.

GelMA, an inexpensive cell-responsive biomaterial derived from denatured collagen, is also suitable for cell-laden micro-tissues, as it supports cell adhesion, proliferation, and migration in both cell seeding and encapsulation applications. Similar to MeHA, by modifying the degree of methacrylation, the hydration and mechanical properties of GelMA can be tuned. A photoinitiator may be used to improve polymerization efficiency. A recently discovered photoinitiator, lithium phenyl-2,4,6-trimethylbenzoylphosphinate (LAP), has demonstrated advantages over more commonly used photoinitiators such as 12959. LAP offers greater water solubility, higher polymerization efficiency with a 365 nm light source, and minimal cytotoxicity. Moreover, LAP has significant absorbance above 400 nm which allows efficient polymerization using visible light, thereby reducing the potential for UV damage. HPCs were harvested and resuspended in a 5 wt % GelMA macromer solution and/or 1 wt % MeHA solution (plus 5 mM RGDS to enhance cell adhesion) with 0.1 wt % LAP as photoinitiator. The selection of macromer concentration is based on the mechanical properties of native liver tissue. HPCs are encapsulated in the 3D scaffold described above. The cell density in the gels is optimized from 1 million per mL to 15 million per mL, according to published protocols. (See, e.g., V. Liu Tsang, et al, "Fabrication of 3d hepatic tissues by additive photopatterning of cellular hydrogels", Faseb J. 2007;21:790-801.)

After fabrication, constructs are gently rinsed with saline solution and immersed in hepatocyte media. Cell viability is monitored progressively with time, e.g., at day 1, 7, 21 and 30, via live-dead staining using calcein AM and ethidium homodimer to measure the percentage of cells that remain viable. In this procedure, cell-laden hydrogels stained with a solution of calcein AM (2 µg/ml) and ethidium homodimer (4 µg/ml Molecular Probes) for 30 min at normal culture conditions are visualized under a fluorescence microscope. With this assay, live cells stain green while dead cells take up the red dye. The percentage of viable cells inside various hydrogels can be quantitated by ImageJ software from the National Institutes of Health. Alternatively or in parallel, cell viability and proliferation can be assessed by a DNA assay (CyQuant, Molecular Probes). To monitor the growth of cells, DNA assays can be performed to estimate the total number of cells. DNA samples at progressive intervals, e.g., from days 7, 21 and 30, are taken and compared to samples from day 1 to assess cell proliferation and death.

Characterization of hepatic function may include assessments of albumin (ALB) secretion urea synthesis, and phenotypic expression of hepatic nuclear factor 4a (HNF4a), glucose-6-phosphatase (G6D) and multidrug resistance-associated protein 2 (MRP 2).

EXAMPLE 1

Evaluation of Hepatic Maturation and Function

The maturation and function of HPCs in the 3D scaffold can be systematically evaluated by commonly-used assays. The gene expression of ALB, HNF 4α, G6D, and MRP 2 are assessed by real time PCR at days 3, 7, 21 and 30. Albumin secretion and urea synthesis may also be monitored at the same time points to further confirm hepatic maturation. ELISA is used to quantify the albumin secretion at each time point. Commercially available kits (Sigma-Aldrich, Inc.) can be used to measure the urea concentration in the culture at the same time points.

After confirming hepatic maturation, further tests on hepatic function may be performed. Gluconeogenesis can be probed using periodic-acid Schiff (PAS) staining. Cytochrome P450 enzymatic activity, which plays an important role in detoxification processes, can be determined via P450-Glo™ CYP450 Assays (Promega). Formation of bile canaliculi is characterized as well at day 7, 21 and 30. After three washes with phenol-red free media, the 3D cultures were incubated with 2 µg/mL CDF [5-(and-6)-carboxy-2', 7'-dichlorofluorescein diacetate, Molecular Probes] for 30 minutes, and washed three times again prior to examination with fluorescence microscopy (excitation/emission wavelengths: 495/520 nm). CDF was endocytosed by hepatocytes, cleaved by intracellular esterases, and excreted by transporters into the bile canaliculi between hepatocytes.

Since both GelMA and MeHA are biodegradable materials, significant degradation may be encountered, especially during long-term culture. To modulate the degradation rate, the non-degradable biocompatible polymer poly(ethylene glycol) diacrylate (PEGDA) is added to the prepolymer solution. Prior work has demonstrated that even a small amount of PEGDA can effectively delay the degradation.

EXAMPLE 2

Optimization of Co-culture Conditions

The liver consists of multiple cell types, such as hepatocytes, endothelial cells, and fibroblasts, working together to provide hepatic functionality. For hepatic cultures in vitro, it has been widely recognized that co-cultures with other supportive cells, e.g., endothelial cells, fibroblasts, and MSCs, can significantly stabilize hepatic phenotype and function. In order to achieve the most successful co-culture system, optimization of culture conditions (e.g., combination of culture media) should be performed both in 2D and 3D contexts prior to incorporating cells within the complex 3D scaffold. In prior studies and preliminary tests, co-cultures of MSCs and endothelial cells with hepatocytes are well supported in hepatic media.

Vascularization is vitally important for tissues with highly active metabolism, such as the heart and liver due to their intensive demand of oxygen and nutrient supply as well as waste disposal. By incorporating ECs and the right geometrical cues (i.e., the channel and conduit structures) in the 3D scaffold, proper vascularization can be achieved to construct a micro-liver model for capable of performing hepatic functions.

Polymer Particles as HFPs

In this embodiment of the liver-mimetic device, polydiacetylene (PDA) nanoparticles may be used to attract, capture and sense pore-forming toxins PFTs when installed in a precise 3D matrix of PEGDA hydrogel with modified liver lobule configuration generated using the above-described dynamic optical projection stereolithography (DOPsL).

Figure 8A:
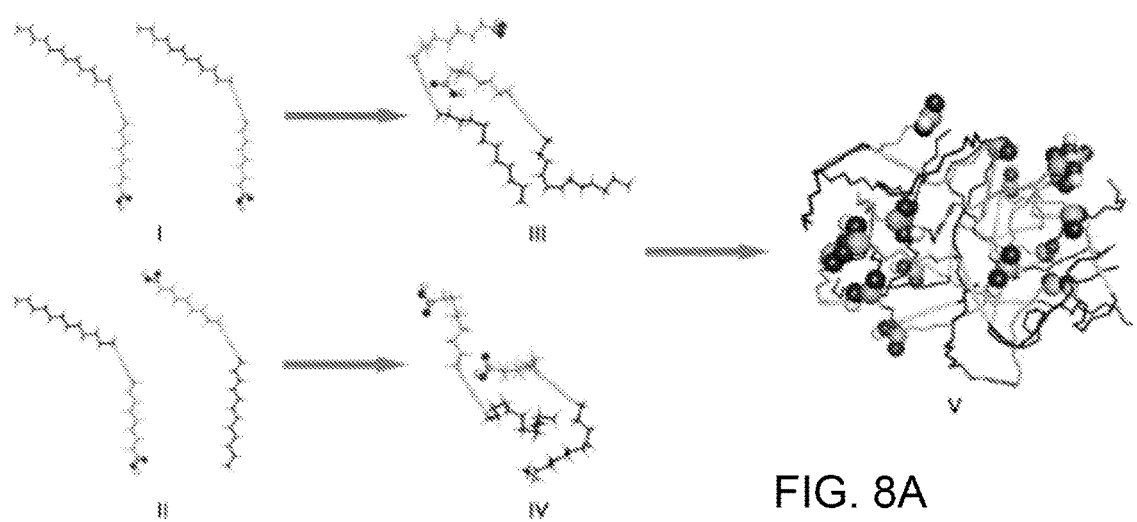
FIG. 8A is a computer simulation showing preparation of PDA nanoparticles derived from self-assembly of PCDA.

The PDA nanoparticles are derived from self-assembly of 10, 12-pentacosadiynoic acid. FIG. 8A provides a computer simulation of the PCDA self-assembly process. Two different initial conformations were arranged for a cluster consisting of 2 PCDAs: head-head parallel (I) and head-tail parallel (II). In the simulation, PCDAs in a head-head parallel arrangements moved closer together, with their polar heads pointed in one direction and their hydrophobic tails pointed in the other direction. In (III), the PCDAs in the head-tail parallel arrangement approached each other ending up in a similar conformation (IV) to that of (III). Thus, it can be demonstrated that the initial conformation of PCDA cluster has little influence on the final simulated conformation. Another PCDA cluster consisting of 16 PCDAs was constructed by sequentially merging two 2-PCDA clusters, then 4-PCDA clusters and, finally, two 8-PCDA clusters. After the simulation, the polar heads of PCDAs were all exposed to solvent and their hydrophobic tails tended to be hidden within the inner structure of the cluster (V).

Figure 8B:
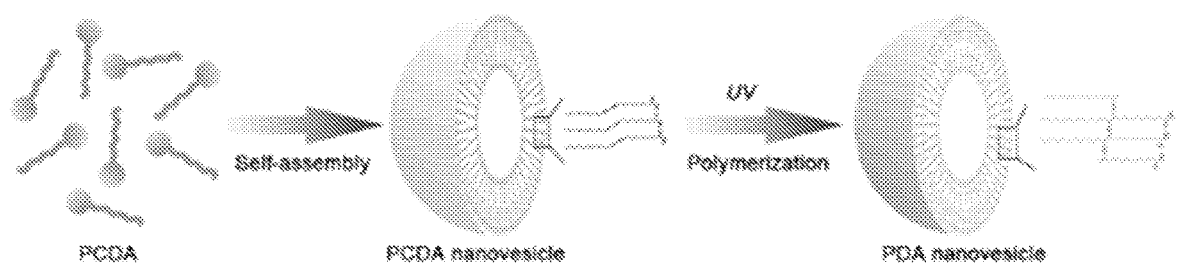
FIG. 8B is a schematic presentation of an exemplary preparation scheme for PDA nanoparticles.

FIG. 8B illustrates a preparation scheme for PDA nanoparticles. In the first step shown at the left of the figure, assisted by sonification, PCDA was self-assembled into nanovesicles, so that the PCDA was closely packed and properly ordered. In the next step, colorless PCDA nanovesicles undergo polymerization via a 1,4-addition reaction to form alternating ene-yne polymer chains upon irradiation with 254 nm UV light, creating blue vesicle-structured PDA nanoparticles with a characteristic absorption peak at around 640 nm.

Figure 9A:
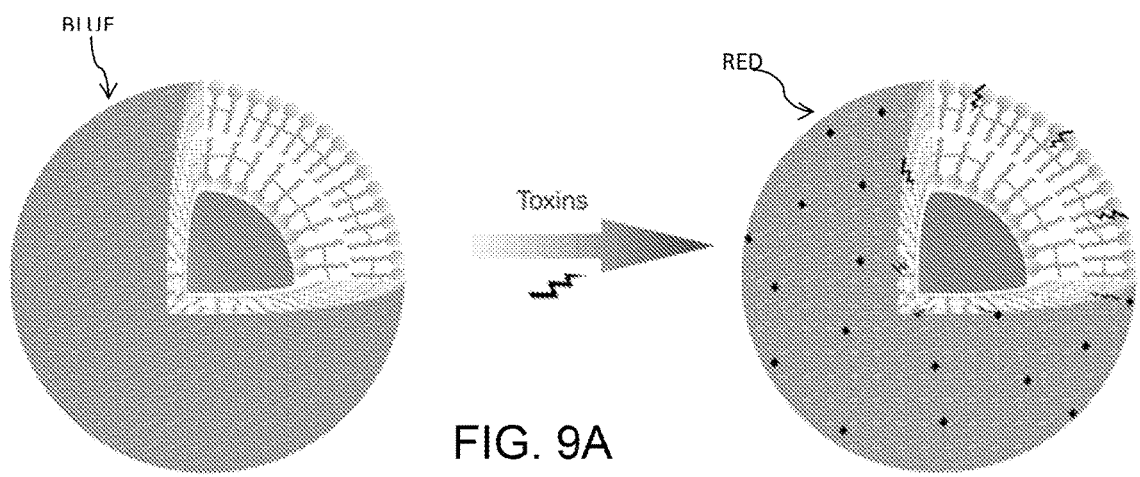
FIGS. 9A-9D diagrammatically illustrate the function of PDA nanoparticles as "nanotraps" to attract, capture, and sense toxins, where FIG. 9A provides a schematic presentation of the interaction between PDA nanoparticles and toxins.

The nanoparticle surface is made of a π-conjugated polymer with alternating double- and triple-bond groups in the main polymer chain. The cell membrane-mimicking surface functions to attract, capture and neutralize toxins due to the interactions between PDA and toxins. Binding toxins to PDA nanoparticles disrupts the extensively delocalized enyne backbones of molecularly ordered PDA side chains, thus inducing a fluorescence enhancement (none-to-fluorescence) as well as color change (blue-to-red), as schematically illustrated in FIG. 9A.

Figure 9B:
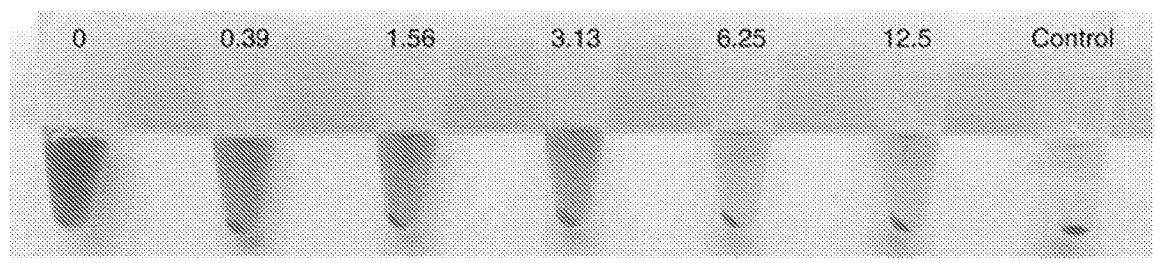
Figure 9C:
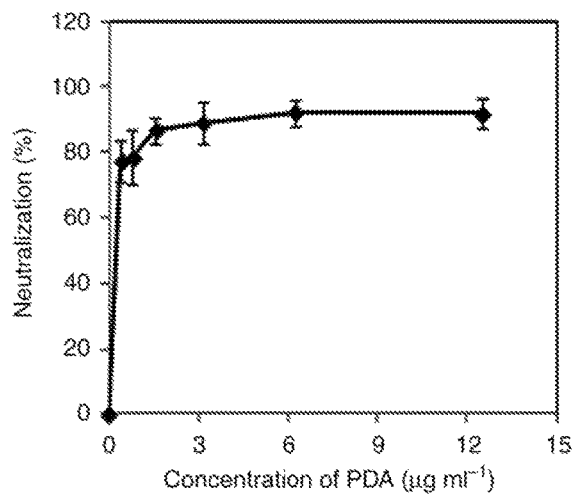

The ability of PDA nanoparticles to capture and neutralize toxins was evaluated by a red blood cell (RBC) lysis test. A widely studied PFT, melittin, the principal toxic component of bee venom, was mixed with PDA nanoparticles and added to murine RBCs. The centrifuged RBC solution was incubated with normal saline (as a control) or melittin mixed with PDA nanoparticles at different concentrations, as shown in FIG. 9B. Qualitatively, melittin mixed with more PDA nanoparticles produced a clearer supernatant, indicating that fewer RBCs were damaged. The neutralization efficiency was quantified via colorimetric readings, shown in FIG. 9C. The results show that PDA nanoparticles can capture and neutralize melittin in vitro. The melittin-binding capacity of PDA nanoparticles is higher than 1 mmol $g^{-1}$. This capacity is greater than that of previously reported protein-adsorbing films, nanofibers and nanoparticles. The neutralization efficiency of PDA nanoparticles is ~92%.

Figure 9D:
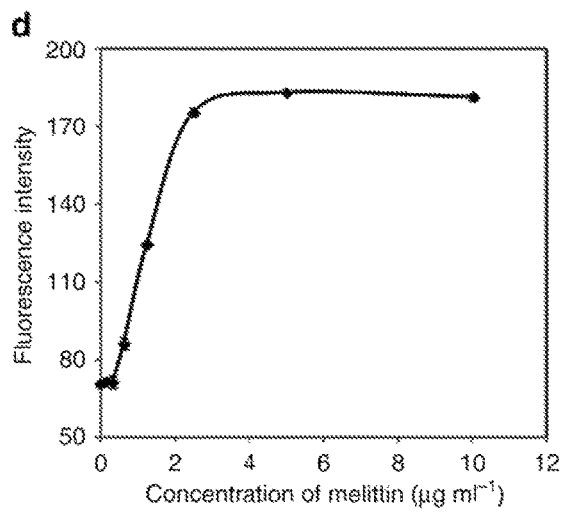
Figure 9E:
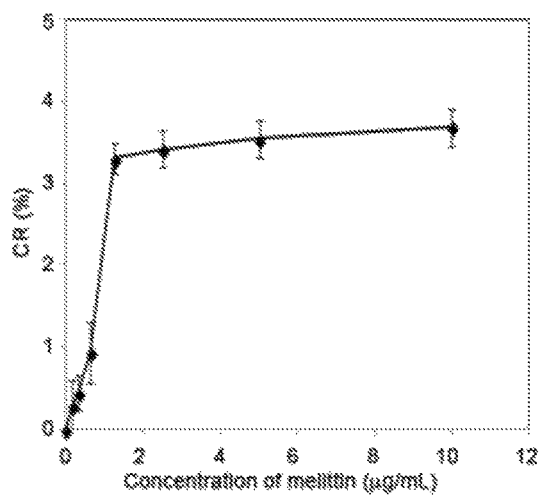
FIGS. 9E and 9F show melittin induced chromatic shift of PDAs, where FIG. 9E plots the color response (CR) of PDA nanoparticles exposed to melittin at different concentrations.
Figure 9F:
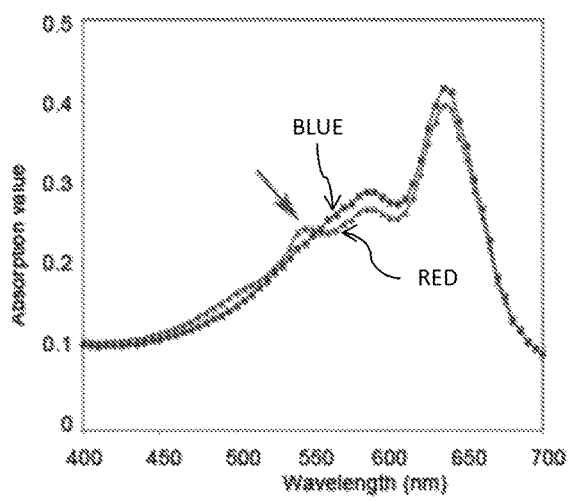

The ability of PDA nanoparticles to sense toxins was also studied. As shown in FIG. 9D, the interaction between melittin and PDA significantly enhanced the red fluorescence of PDA nanoparticles. The red fluorescence intensity of PDA increased with the concentration of melittin. Meanwhile, the binding of melittin can also induce a slight color change of PDA nanoparticles. FIG. 9E shows the color response (CR) of PDA nanoparticles exposed to melittin at different concentrations. FIG. 9F provides the absorption curves of initial PDA nanoparticles ("blue" line) and melittin-incubated PDA nanoparticles ("red" line). The arrow indicates the slight color shift from blue to red. By using the fluorescence data, the binding constant between melittin and PDA nanoparticles was calculated as 630 $M^{-1}$ from Langmuir isotherm. Compared with recently reported nanoparticles with 100% neutralization of melittin (see, e.g., Hoshino et al., "The rational design of a synthetic polymer nanoparticle that neutralizes a toxic peptide in vivo", Proc. Natl Acad. Sci. USA 109, 33-38 (2012).), the PDA nanoparticle has a lower binding constant, which may be one of the reasons why PDA nanoparticles cannot achieve 100% neutralization of melittin.

Figure 10:
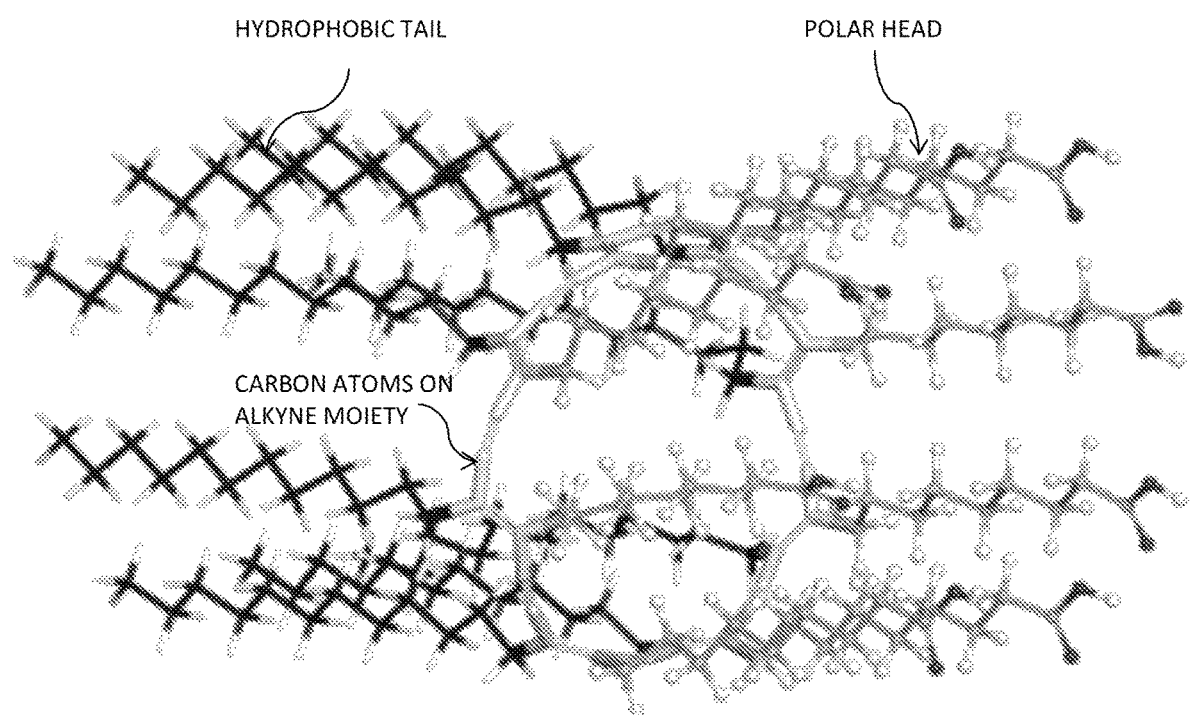
FIG. 10 illustrates the computer simulated structure of PDA.

To better understand the interaction between PDA nanoparticles and melittin, computer simulations were performed at the molecular level. The simulation was constructed using Discover Studio 3.1 and optimized in Hyperchem workspace, with the degree of polymerization set as 8. The optimized structure of PDA is shown in FIG. 10, where the hydrophobic tail, polar head and carbon atoms on the alkyne moiety are labeled.

Figure 11A:
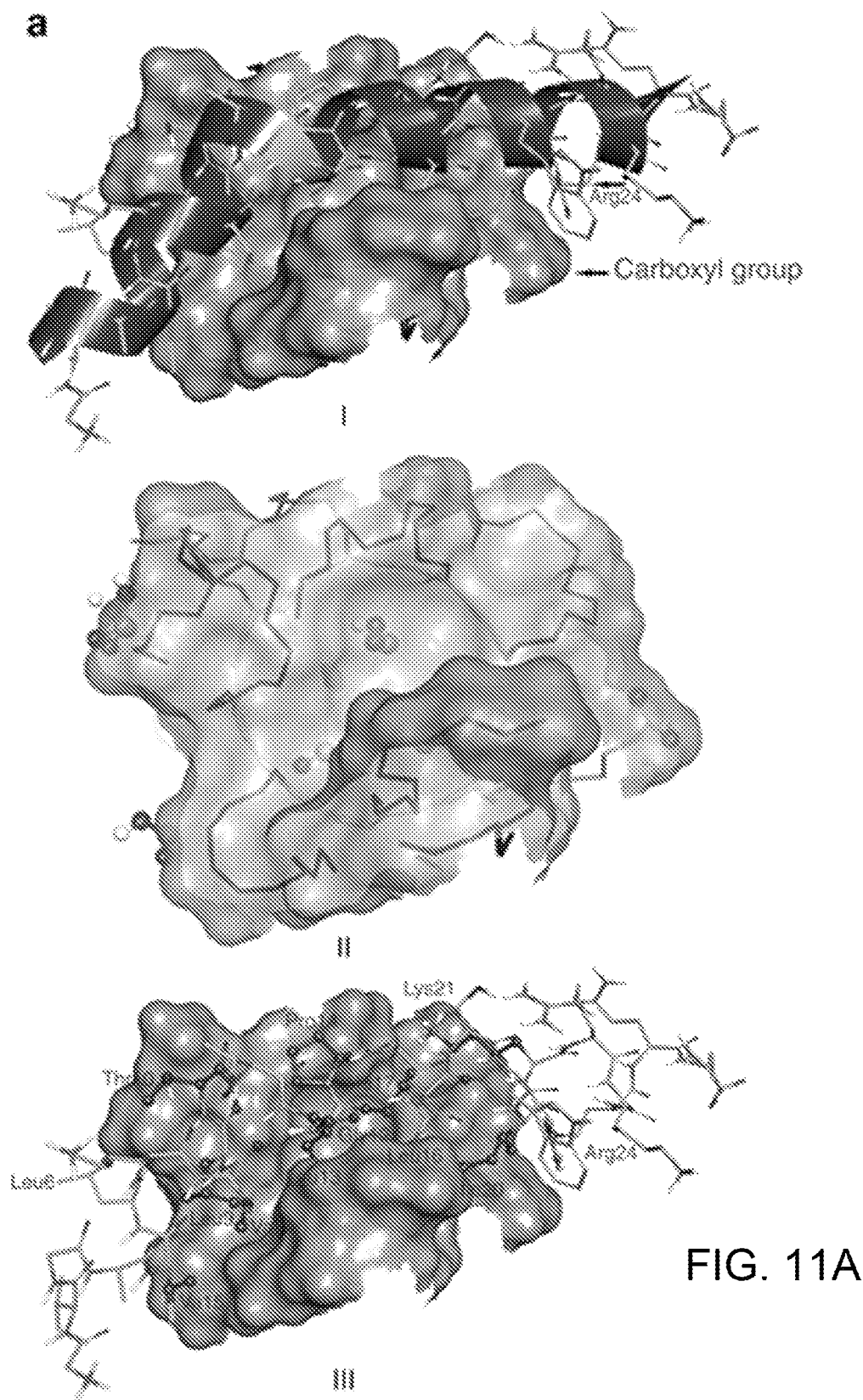
FIGS. 11A-11C are computer simulations of the interactions between PDA and melittin.
Figure 11B:
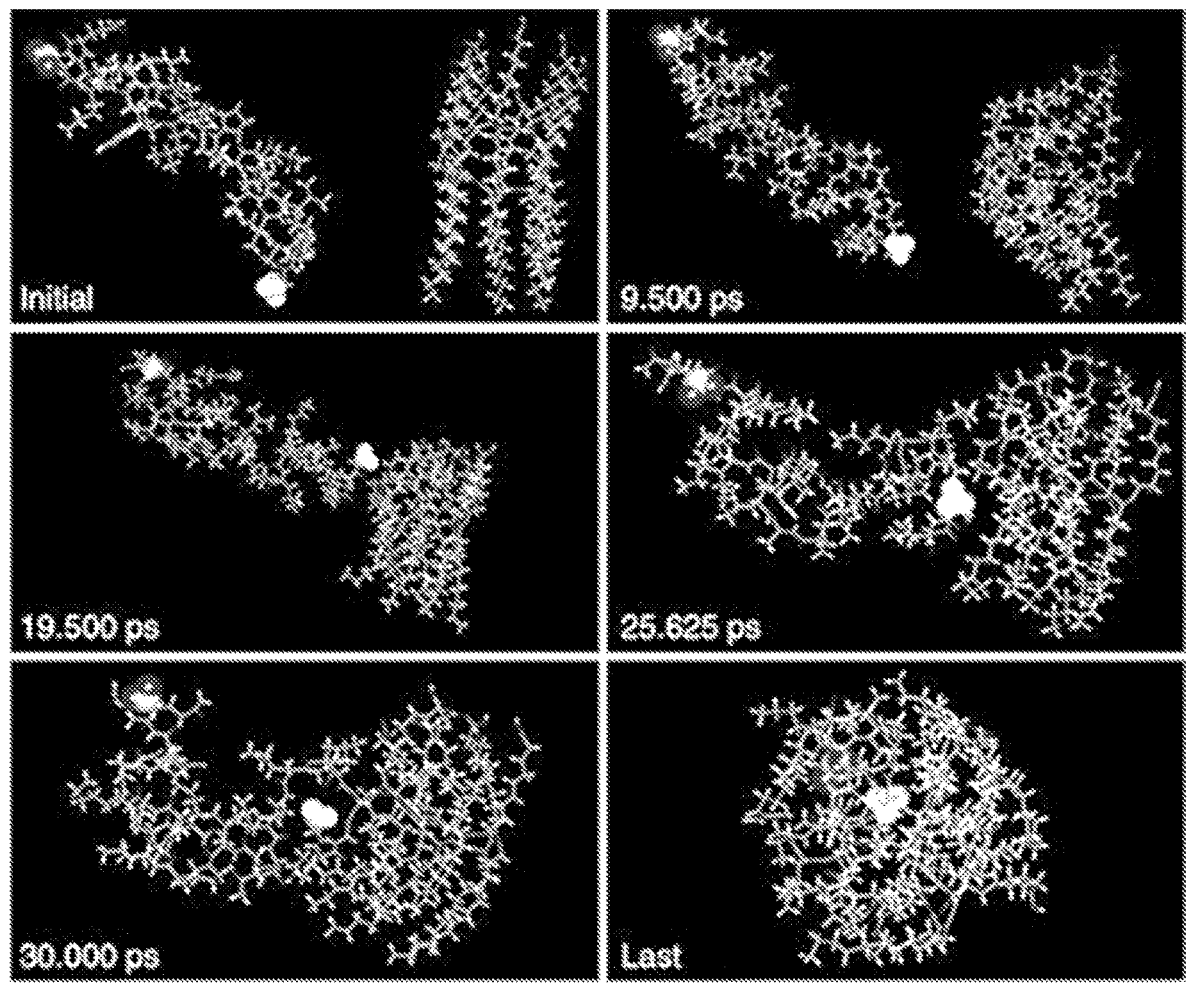
Figure 11C:
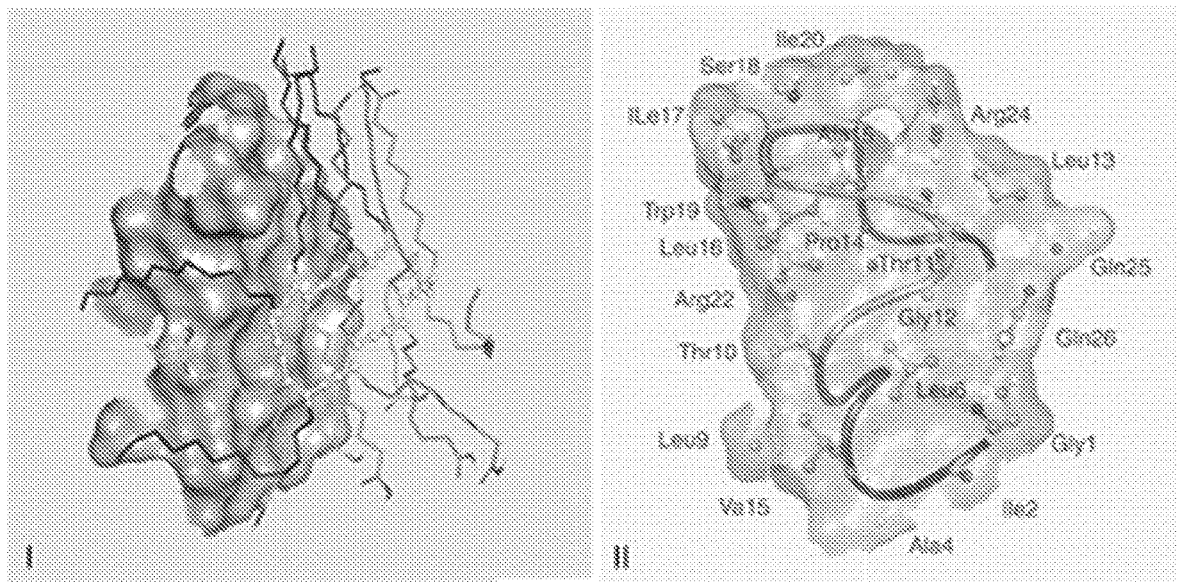

After docking PDA to melittin, nine conformations of complex composed of melittin and PDA were obtained. For all of these conformations, the binding affinities between the two components of the complex are negative, suggesting that PDA possesses the capability to bind melittin. The conformation on the top of the list (FIG. 11A, I) has the most negative binding affinity: −1.8 kcal $mol^{-1}$. In this conformation, PDA interacts with melittin via its hydrophobic tails (seven, in total) and one polar head (FIG. 11A, II). On the other hand, half of 26 residues in melittin interact with PDA. Among these residues, only Thr10, Lys21 and Arg24 are polar residues (FIG. 11A, III). An electrostatic interaction between the carboxyl group of one polar head in PDA and the guanidine part of Arg24 in melittin was also observed (FIG. 11A, I). The interactions between PDA and melittin were further studied by performing simulated annealing using molecular dynamics (MD). MD simulation can enable a modelled system to surmount small energy barriers on the potential surface and locate sites of lower potential energy, while dynamic annealing can obtain a minimum energy. As illustrated in FIG. 11B, PDA and melittin adjusted their orientations and approached each other in the simulation, followed by forming a complex, suggesting that PDA can attract melittin in close proximity, followed by capture. In FIG. 11B, the carboxy terminal and amino terminal of melittin are highlighted. It was determined that interaction with melittin can affect the conformation of PDA, which may explain experimental findings of fluorescence enhancement and color change of PDA after incubation with melittin. The last conformation of the modelled system (labeled "LAST") experienced simulated annealing and subsequent equilibrium. Moreover, by simulated annealing using MD, the PDA-melittin interaction mode could be obtained. In FIG. 11C, I shows PDA on the interaction interface, while II shows the interaction mode of melittin to PDA. On the basis of these simulations, one can conclude that hydrophobic and electrostatic interactions exist between PDA and melittin, and the former interaction contributes much more than the latter, thus enabling PDA nanoparticles to capture PFTs.

After confirming the PDA nanoparticles' ability to attract and capture melittin in solution, a 3D device consisting of a biomaterial hydrogel scaffold was constructed using the DOPsL printing process described previously. A photocrosslinked poly(ethylene glycol) diacrylate (PEGDA) hydrogel was used as a 3D matrix. PEGDA is often used in biomedical applications because it is non-toxic, non-immunogenic, favorable to nutrient and oxygen transport, and tunable in its mechanical properties. To chemically link PDA nanoparticles into the networks of PEGDA hydrogel, a diacetylene derivative called PCDA-acrylamide (PCDA-A 5) was synthesized according to the scheme shown in FIG. 12.

Figure 12:
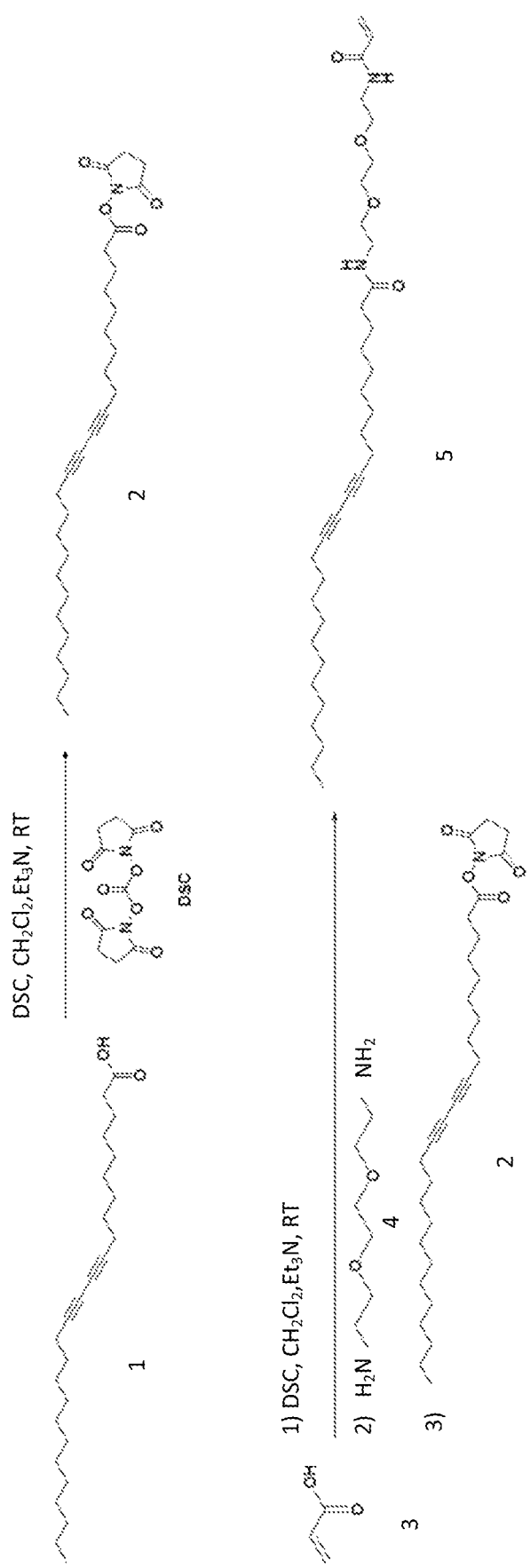
FIG. 12 shows the synthesis scheme for PCDA-A.

Referring to FIG. 12, In a 50-ml flask with a stir bar, compound 1 (PCDA, 374 mg, 1.0 mmol) was dissolved in dry CH2Cl2 (10 ml) followed by addition of triethylamine (101 mg, 1.0 mmol) and N,N'-disuccinimidyl carbonate (256 mg, 1.0 mmol). The reaction solution was stirred at room temperature for 1 h to activate compound 1, creating active ester 2. Then, acid 3 (74 mg, 1.0 mmol) was dissolved in dry $CH_2Cl_2$ (10 ml), followed by adding triethylamine (101 mg, 1.0 mmol) and N,N'-disuccinimidyl carbonate (256 mg, 1.0 mmol). The resulting solution was stirred at room temperature for 1 h, and then amine 4 was added. The reaction solution was monitored by liquid chromatography-mass spectrometry. Four hours later, ester 2 was added. The reaction was stirred at room temperature for 4 h, product 5 (PCDA-A 5) was found by liquid chromatography-mass spectrometry analysis. The reaction solution was evaporated and the residue was purified by flash column chromatography to produce 84 mg compound 5 as white solid. The yield was 15%. The PCDA-A 5 was identified by $^1$H NMR, $^{13}$C NMR and high resolution mass spectrometer.

To prepare the PDA nanoparticles, 40 mg of PCDA was added into 8 ml of distilled water, followed by probe sonication for 5 min at ~75° C. The solution was stored overnight at 4° C. Finally, the solution was irradiated with ultraviolet light for 5 min in an ice bath, creating blue and non-fluorescence PDA nanoparticles. PCDA-A 5 and PCDA mixed nanoparticles were prepared by sonication of the mixed PCDA-A 5 and PCDA (mass ratio 1:19) in hot water (at about 75° C.). PCDA-A 5 is based on the diacetylene moiety of PCDA with an extended ethylene oxide spacer arm and an acrylamide functional head group. By mixing PCDA and PCDA-A 5, the resulting nanoparticles possess an acrylamide group on its surface, shown diagrammatically in FIG. 13A, and can be chemically tethered to the PEGDA hydrogel through addition polymerization, shown in FIG. 13B.

Figure 13C:
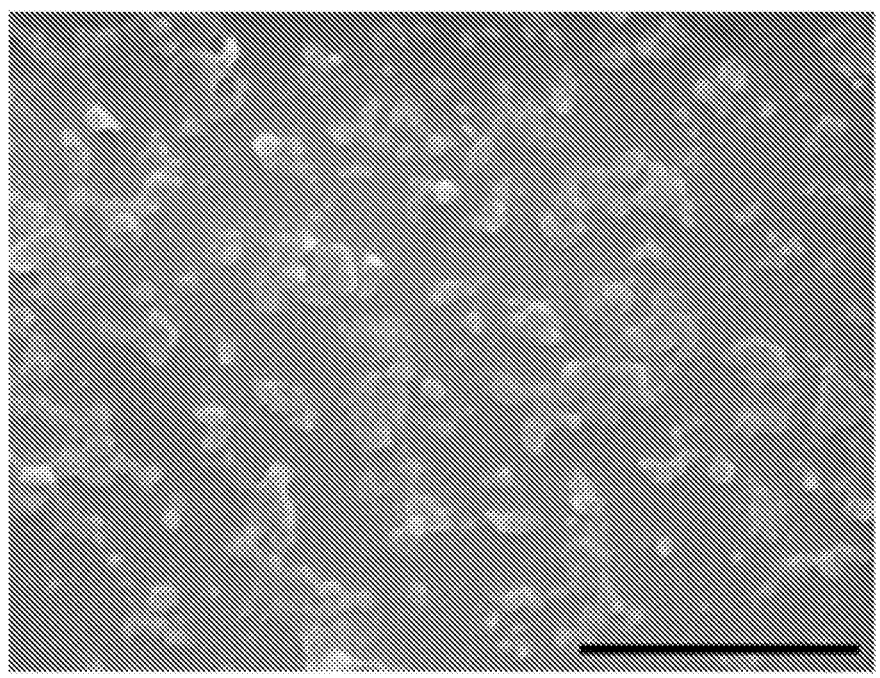
Figure 14A:
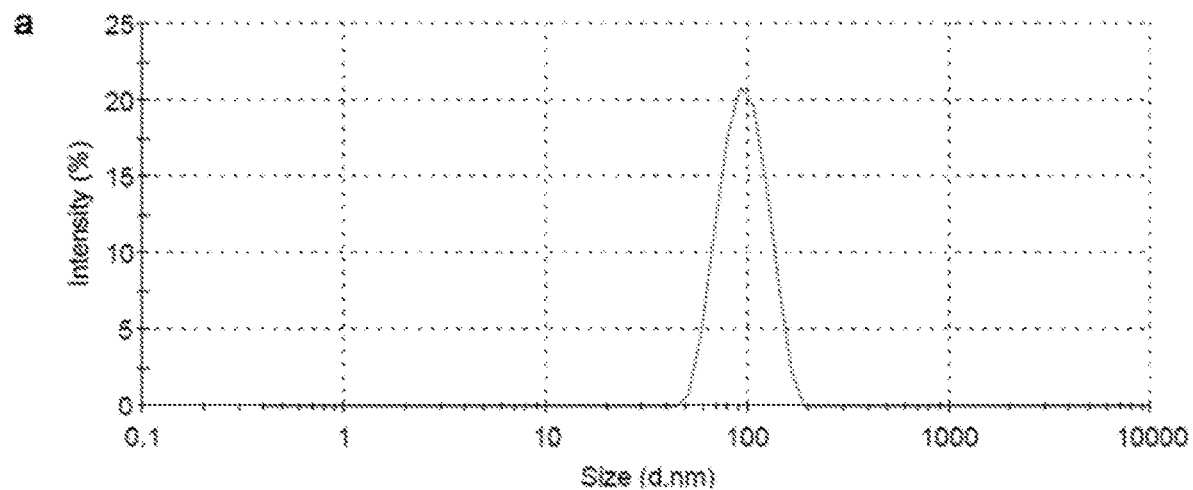
FIGS. 14A and 14B illustrate the particle size and zeta potential of PCDA-A and PCDA composite nanoparticles, respectively.
Figure 14B:
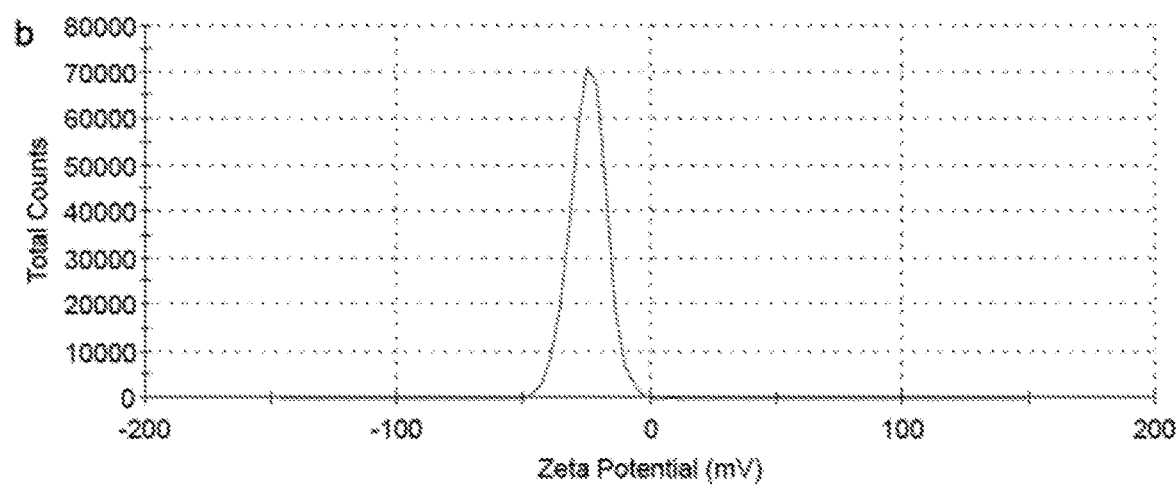
Figure 15:
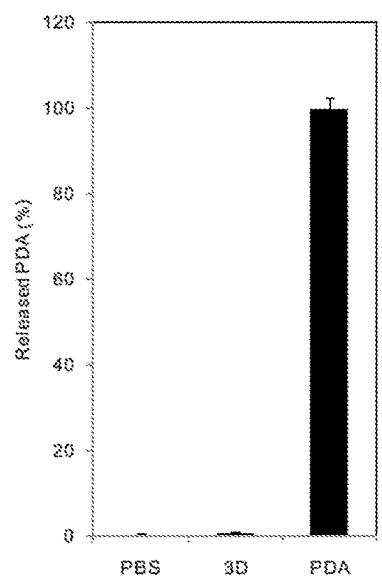
FIG. 15 plots the comparative nneutralization efficiency of an embodiment of the liver-mimetic detoxification device.

The nanoparticles have a mean particle size of ~100 nm according to the scanning electron microscope image shown in FIG. 13C. The particles' distribution was determined by dynamic light scattering, as shown in FIG. 14A. The nanoparticles have a mean particle size of 110 nm with polydispersity index of 0.23. Meanwhile, the nanoparticles have a zeta potential of ~25 mV (FIG. 14B). Due to the extremely slow degradation rate of PEGDA network, once chemically immobilized in PEGDA hydrogel, it is difficult for PDA nanoparticles to release into the solution. As indicated by measuring absorbance $A_{3D}$ of the supernatant at 640 nm, plotted in FIG. 15, no significant amount of PDA nanoparticles was released from the PEGDA hydrogel after incubation of the 3D liver-mimetic device in PBS for 24 h. Controls for 0 and 100% release consisted of PBS ($A_{0\%}$) and a solution of the same amount of PDA nanoparticles in the 3D liver-mimetic device ($A_{100\%}$), respectively. The percentage of released PDA nanoparticles was calculated by $(A_{3D}-A_{0\%})\times(A_{100\%}-A_{0\%})^{-1}\times 100\%$.

The liver-mimetic structure with modified liver lobule topology allows the toxin to reach the center of the matrix quickly, as shown in FIG. 1C. The modified structure has a higher specific surface area than the typical liver lobule structure shown in FIG. 1B, which allows toxins to enter the 3D structure effectively. Sliced images of the 3D model were loaded to the DMD chip to continuously generate optical patterns and expose the photopolymerizable material in a layer-by-layer manner. The DMD chip used in the experimental system was a DLP-07 XGA from DLP Technology of Texas Instruments. The mask patterns, examples of which are the pair shown in FIG. 3B, were alternatively printed by the DOPsL method layer-by-layer, to fabricate 3D PEGDA hydrogels with precise microstructures.

PEGDA (20 wt %) in $H_2O$ with 1% lithium phenyl-2,4, 6-trimethylbenzoylphosphinate was mixed with PDA particles suspension (5 mg ml$^{-1}$) in an equal volume ratio. The mixture was then loaded to the sample stage of the DOPsL system and polymerized via patterned ultraviolet exposure to fabricate corresponding 3D structures. After the PDA nanoparticles were immobilized, the 3D structure was incubated in PBS for 2 h at 37° C., and then irradiated by ultraviolet for 5 min to allow the polymerization of PDAs. The multilayer microstructure with modified liver lobule topology is shown in FIG. 3D, where the scale bar is 50 µm.

As a proof of concept, PEGDA hydrogels with and without PDA nanoparticles were fabricated into simple 3D cylinders and subsequently incubated with melittin solution (50 µg ml$^{-1}$). Initially, the control PEGDA hydrogel (without nanoparticles) was transparent and non-fluorescent. No color or fluorescence changes were detected after incubation with melittin. In comparison, PDA nanoparticles incorporated hydrogel appeared opaque without fluorescence initially. After incubation with melittin solution (50 µg ml$^{-1}$), however, the composite hydrogel cylinder emanated red fluorescence, which gradually diffused from the surface to the inner part in a time-dependent manner, indicating successful binding of melittin to PDA.

Figure 16:
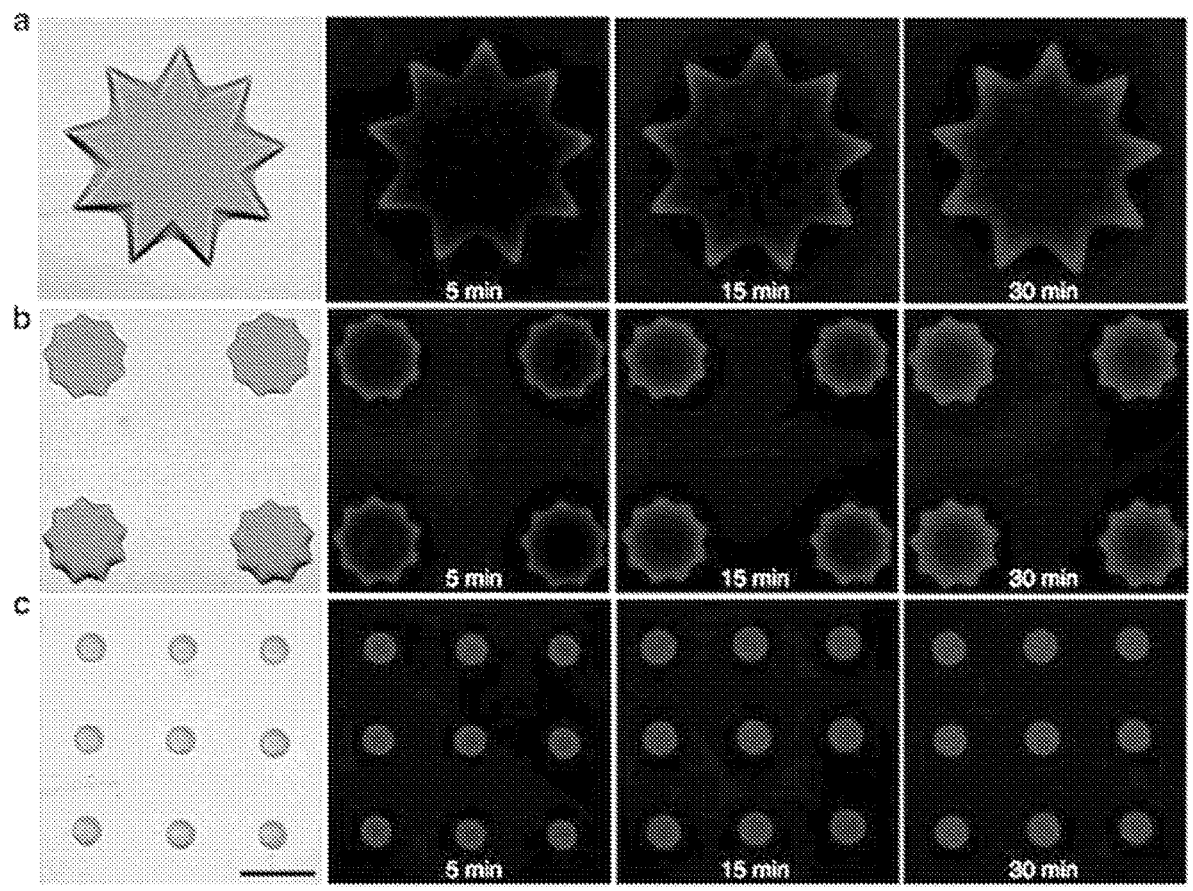
FIG. 16 illustrates the effect of different surface patterns on capturing toxins by the 3D-patterned PEG hydrogel encapsulated with PDA nanoparticles. The scale bar is 200 μm.

To evaluate the effect of the hydrogel's specific surface area on the efficiency of capturing toxins, three types of 3D posts were fabricated with the same flower-like projection and length but different diameters, shown in FIG. 16, where the thinner post (c) displayed higher specific surface area. Melittin gradually diffuses into each post, regardless of the diameter, however the rate of diffusion varies. Over the same periods, red fluorescence can only be detected on the outer area of the thicker posts while in the thinner posts, the fluorescent signals were also observed in the inner region. On the basis of the previous data that the fluorescent signals correspond to PDA-melittin interaction, the fluorescent signal trends that were observed could imply a modulation of PDA-melittin interactions based on the specific surface area. The 3D structure containing PDA nanoparticles with a higher specific surface area may be more efficient in enriching toxins. In addition, macromolecules with a higher molecular weight diffuse slower into the PEGDA hydrogel, suggesting that physical properties such as the porosity of the hydrogel can affect the diffusion of molecules into PEGDA hydrogel, and the PEGDA hydrogel may allow melittin to diffuse faster into the inner structure compared with others macromolecular proteins in the plasma.

To test the capability of PDA-based liver mimetic device to capture toxins, a comparison was run between the device and a slab control with the same total volume. Neutralization of the haemolytic activity of melittin by PDA nanoparticles was assayed by a modified standard haemolytic assay procedure. Melittin (final concentration in RBC suspension was 5 µg ml$^{-1}$) was pre-incubated with the same volume of PDA nanoparticles for 30 min at 37° C. in PBS. The melittin/NP mixture (100 µl) was then added to the RBC solution (2% v/v, 100 µl), followed by incubation at 37° C. for 30 min. Samples were then centrifuged at 800 g for 5 min. The release of haemoglobin was measured by bicinchoninic acid kit. Controls for 0 and 100% neutralization of haemolytic activity consisted of RBCs incubated with 5 µg ml-melittin (A0%) and a RBC suspension with normal saline (A100%), respectively. The percentage of neutralization was calculated according to equation (1):

For the liver-mimetic 3D PDA nanoparticle-enabled detoxifier, 50 µl of melittin (50 µg ml$^{-1}$) was pre-incubated in the device for 60 min at 37° C. Then, the melittin solution was carefully collected by directly pipetting the melittin solution and washing the device with 200 µl PBS. The resulting 250 µl solution was then added to a 250 µl RBC solution (4% v/v), followed by incubation at 37° C. for 30 min. Finally, the percentage of neutralization was calculated as:

$$\text{Neutralization}(\%) = (A_{sample} - A_{0\%}) \times (A_{100\%} - A_{0\%})^{-1} \times 100.$$

The neutralization efficiency of the 3D liver-mimetic device was compared with that of the equivalent amount of PDA nanoparticles or PEGDA hydrogel.

Figure 17A:
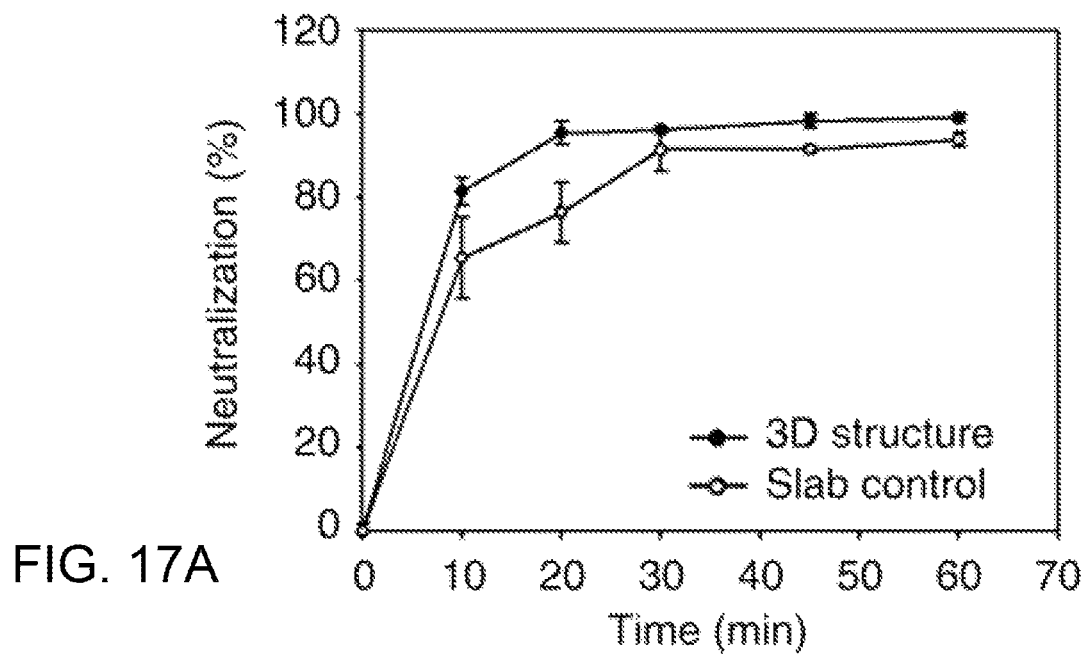
FIG. 17A is a plot comparing the neutralization efficiency over time between the liver-mimetic structure and a slab control.
Figure 17B:
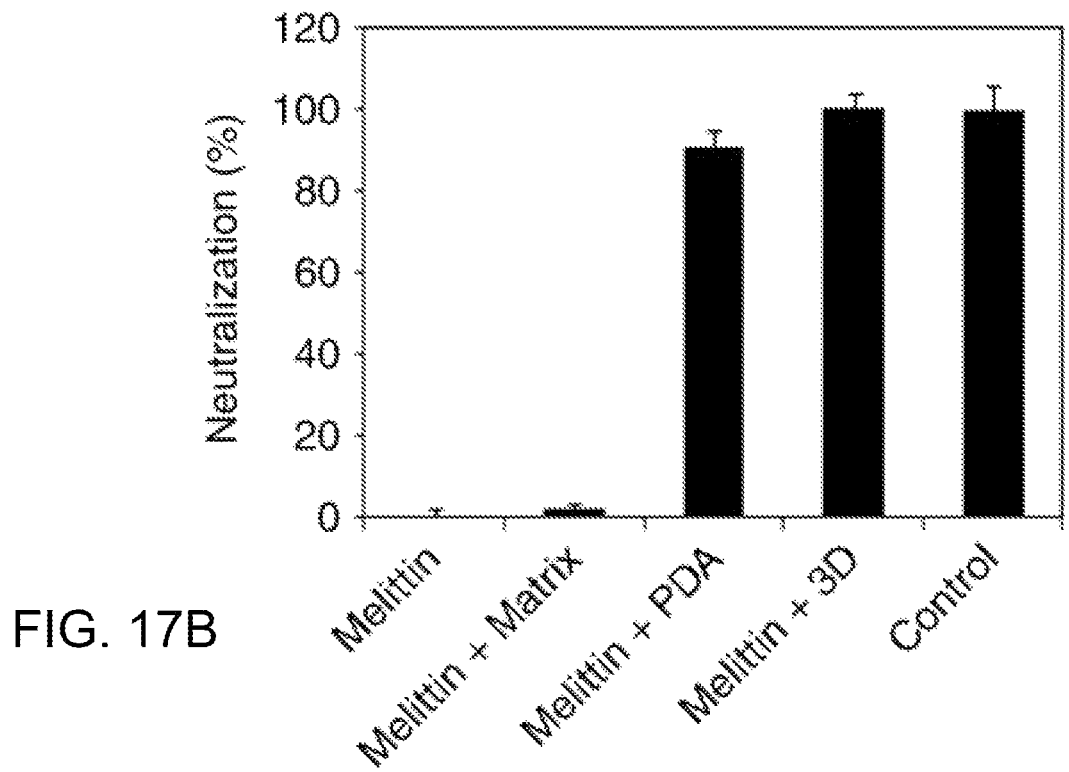
FIG. 17B is a plot comparing the neutralization efficiency for the liver-mimetic structure with PDA particles against the matrix and particle separately.

As shown in FIG. 17A, compared with the slab, the liver-mimetic structure neutralizes toxins much more rapidly as a result of the faster diffusion of toxins into the inner structure. After the incubation of melittin solution, the neutralization efficiency was tested by the haemolytic assay. The RBC solution incubated with melittin treated by the liver-mimetic device exhibits a clear supernatant similar to that of the saline control. As illustrated in FIG. 17B, the liver-mimetic device (4th column) achieved 100% neutralization of toxins (equal to the saline control—5th column) while the equivalent amount of free PDA nanoparticles (3rd column) neutralized 91% of toxins. The PEGDA hydrogel matrix alone (2nd column) has little capacity for neutralizing toxins. Thus, the biomimetic detoxifier comprising a 3D matrix with embedded PDA nanoparticles demonstrates clear effectiveness in neutralizing toxins.

A major benefit of the liver-mimetic devices described herein include the early drug testing of new drugs in the drug discovery process. Use of such a device could markedly reduce the number of drug failures at the clinical stage and thus reduce the high cost of drug development, now a major economical roadblock to sustained progress in healthcare. The patient-specific liver-on-a chip model according to some embodiments of the invention may provide a reliable and cost-efficient in vitro platform to facilitate drug metabolism studies, preclinical drug screening, and fundamental hepatology research. Some embodiments of the liver-mimetic device provide a novel strategy for designing nanoparticle-enabled detoxification treatments. In this latter embodiment, the cell-free nature of device allows integration of a variety of functionalities and nanoelements in rationally designed microarchitectures. This could lead to many breakthroughs in the development of future detoxification platforms.

The invention claimed is:

1. A method for in vitro simulation of a hepatic function on a material, comprising:
    suspending biological hepatic-functioning particles (bHFPs) in a prepolymer and photopolymerizing the prepolymer by bioprinting using maskless dynamic optical projection stereolithography (DOPsL) to form a biomimetic 3D polymer scaffold comprising a matrix of liver-like lobules encapsulating the bHFPs therein, the matrix comprising a plurality of layers of honeycomb patterns with channels and central conduits;
    printing supportive cells onto the matrix using DOPsL to spatially localize the supportive cells to align in the channels and central conduits to spatially control cell-cell interactions between the bHFPs and the supportive cells; and
    exposing the matrix to the material, wherein the matrix mimics a tissue with bHFPs and supportive cells in three dimensions.

2. The method of claim 1, wherein 3D bioprinting comprises using dynamic optical projection stereolithography.

3. The method of claim 1, wherein each liver-like lobule is hexagonal in structure.

4. The method of claim 1, wherein the bHFPs are hepatic progenitor cells (HPCs) derived from human induced pluripotent stem cells (iPSCs).

5. The method of claim 4, wherein the iPSCs are patient specific.

6. The method of claim 5, wherein the patient specific iPSCs are from subjects having a liver-affecting disease.

7. The method of claim 1, wherein the supportive cells comprise mesenchymal stem cells (MSCs).

8. The method of claim 1, wherein the supportive cells comprise endothelial cells (ECs).

9. The method of claim 1, wherein the prepolymer comprises a methacrylated hyaluronic acid (MeHA).

10. The method of claim 1, wherein the prepolymer comprises a gelatin methacrylate (GelMA).

11. The method of claim 10, wherein the prepolymer further comprises polymer nanoparticles.

12. The method of claim 11, wherein the polymer nanoparticles comprise polydiacetylene.

13. The method of claim 1, wherein the prepolymer comprises poly(ethylene glycol) diacrylate hydrogel (PEGDA).

14. The method of claim 11, wherein the polymer nanoparticles are chemically tethered to the 3D polymer scaffold.

15. The method of claim 1, wherein the hepatic function comprises detoxification.

16. The method of claim 1, wherein the bHFPs are encapsulated within the center portions and the supportive cells are disposed in the channels.

17. The method of claim 16, wherein the bHFPs are co-cultured with additional supportive cells prior to encapsulation into the center conduits.

18. The method of claim 1, wherein the supportive cells comprise endothelial cells (ECs) and mesenchymal stem cells (MSCs).

19. The method of claim 18, wherein the ECs are bioprinted into patterns configured to mimic vascular structures.

20. A method for simulation of a hepatic function on a material, comprising:
    suspending biological hepatic-functioning particles (bHFPs) in a prepolymer solution and photopolymerizing the prepolymer by bioprinting using maskless dynamic optical projection stereolithography (DOPsL) to form a biomimetic 3D polymer scaffold comprising a matrix of hexagonal liver-like lobules encapsulating the bHFPs therein, each lobule having a center portion and a channel surrounding the center portion, wherein the bHFPs are encapsulated within the center portions;
    printing supportive cells onto the matrix using DOPsL to spatially localize the supportive cells to align in the channels and in conduits within the central portions to spatially control cell-cell interactions between the bHFPs and the supportive cells;
    exposing the matrix to the material, wherein the matrix mimics a tissue with bHFPs and supportive cells in three dimensions.

21. The method of claim 20, wherein the co-culture comprises a tri-culture, and wherein the supportive cells comprise endothelial cells (ECs) and mesenchymal stem cells (MSCs).

22. The method of claim 20, wherein the bHFPs are co-cultured with additional supportive cells prior to encapsulation into the center portions.

23. The method of claim 20, wherein the matrix comprises a honeycomb arrangement.

24. The method of claim 20, wherein the bHFPs are hepatic progenitor cells (HPCs) derived from human induced pluripotent stem cells (iPSCs).

25. The method of claim 24, wherein the iPSCs are patient specific.

26. The method of claim 25, wherein the patient specific iPSCs are from subjects having a liver-affecting disease.

27. The method of claim 20, wherein the supportive cells comprise mesenchymal stem cells (MSCs).

28. The method of claim 20, wherein the prepolymer further comprises polymer nanoparticles.

* * * * *